United States Patent
Todoroki et al.

(10) Patent No.: US 11,179,067 B2
(45) Date of Patent: Nov. 23, 2021

(54) BIOLOGICAL STATE MONITORING SYSTEM

(71) Applicant: MINEBEA MITSUMI INC., Nagano (JP)

(72) Inventors: Shinsuke Todoroki, Fukuroi (JP); Shigemi Masuda, Fukuroi (JP)

(73) Assignee: MINEBEA MITSUMI INC., Nagano (JP)

( * ) Notice: Subject to any disclaimer, the term of this patent is extended or adjusted under 35 U.S.C. 154(b) by 13 days.

(21) Appl. No.: 17/050,511

(22) PCT Filed: Apr. 23, 2019

(86) PCT No.: PCT/JP2019/017162
§ 371 (c)(1),
(2) Date: Oct. 26, 2020

(87) PCT Pub. No.: WO2019/208547
PCT Pub. Date: Oct. 31, 2019

(65) Prior Publication Data
US 2021/0085218 A1 Mar. 25, 2021

(30) Foreign Application Priority Data
Apr. 26, 2018 (JP) .............................. JP2018-085690

(51) Int. Cl.
*A61B 5/08* (2006.01)
*A61B 5/113* (2006.01)
*A61B 5/00* (2006.01)

(52) U.S. Cl.
CPC ............ *A61B 5/113* (2013.01); *A61B 5/0816* (2013.01); *A61B 5/6891* (2013.01); *A61B 2562/0252* (2013.01)

(58) Field of Classification Search
CPC .................. A61B 5/113; A61B 5/6891; A61B 2562/0252; A61B 5/08; A61B 5/0816; A61B 5/7203; A61B 5/7207
See application file for complete search history.

(56) References Cited

U.S. PATENT DOCUMENTS 6,719,708 B1 4/2004 Jansen
7,168,429 B2 * 1/2007 Matthews ........... A61M 16/026
128/204.21

(Continued)

FOREIGN PATENT DOCUMENTS

CN 107106085 A 8/2017
JP 61-024010 B 6/1986

(Continued)

OTHER PUBLICATIONS

International Search Report for corresponding International Application No. PCT/JP2019/017162 dated Jul. 23, 2019.

(Continued)

*Primary Examiner* — Andrey Shostak
(74) *Attorney, Agent, or Firm* — Pearne & Gordon LLP

(57) ABSTRACT

There is provided a biological state monitoring system for monitoring biological state of subject on a bed. The system includes at least one load detector and a controller. In a case that the controller determines that body motion is not twitch, the controller ceases to output estimated value of respiratory rate, or outputs first estimated value which is the latest among estimated values obtained in first period, the first period being directly preceding body motion and being determined by the controller to be a period in which subject has no body motion. In a case that the controller determines that body motion is twitch, the controller successively outputs newly obtained estimated values of respiratory rate.

5 Claims, 12 Drawing Sheets

(56) References Cited

U.S. PATENT DOCUMENTS

| | | |
|---|---|---|
| 9,820,680 B2 | 11/2017 | Muzet |
| 10,390,735 B2 | 8/2019 | Akatsu et al. |
| 2009/0221926 A1* | 9/2009 | Younes ............... A61M 16/026 600/529 |
| 2012/0116187 A1 | 5/2012 | Hayes et al. |
| 2014/0088378 A1* | 3/2014 | Muzet ................... A61B 5/681 600/301 |
| 2017/0265815 A1 | 9/2017 | Katsuki et al. |
| 2017/0347948 A1 | 12/2017 | Thein et al. |
| 2018/0146889 A1 | 5/2018 | Akatsu et al. |
| 2018/0206793 A1 | 7/2018 | Akatsu et al. |

FOREIGN PATENT DOCUMENTS

| | | |
|---|---|---|
| JP | 2006-280615 A | 10/2006 |
| JP | 2007-175225 A | 7/2007 |
| JP | 4002905 B2 | 11/2007 |
| JP | 4829020 B2 | 11/2011 |
| JP | 4883380 B2 | 2/2012 |
| JP | 2012-165979 A | 9/2012 |
| JP | 2014-516681 A | 7/2014 |
| JP | 6105703 B1 | 3/2017 |
| JP | 2017-064350 A | 4/2017 |
| JP | 2017-077451 A | 4/2017 |
| JP | 2017-104360 A | 6/2017 |
| WO | 2017/018506 A1 | 2/2017 |
| WO | WO-2017056476 A1 * | 4/2017 ........... A61B 5/6892 |

OTHER PUBLICATIONS

Written Opinion for corresponding International Application No. PCT/JP2019/017162 dated Jul. 23, 2019.
Decision to Grant a Patent for corresponding Japanese Application No. 2018-085690 dated Jan. 24, 2020 and English translation.
English translation of Written Opinion for corresponding International Application No. PCT/JP2019/017162 dated Jul. 23, 2019.
Related U.S. Appl. No. 17/050,292, filed Oct. 23, 2020.
International Search Report for related International Application No. PCT/JP2019/016128 dated Jul. 9, 2019 and English translation.
Written Opinion for related International Application No. PCT/JP2019/016128 dated Jul. 9, 2019 and English translation.
Chinese Office Action dated Apr. 13, 2021 for related Chinese Application No. 201980028293.5 and English translation (previously submitted on IDS dated May 14, 2021 and considered by Examiner on May 19, 2021; Applicant now clarifies that this is a "related" application).
Notice of Allowance dated May 24, 2021 for corresponding Chinese Application No. 201980028227.8 and English translation.
Office Action dated Jun. 10, 2021 for related U.S. Appl. No. 17/050,292.

* cited by examiner

BIOLOGICAL STATE MONITORING SYSTEM

TECHNICAL FIELD

The present invention relates to a biological state monitoring system for monitoring a biological state of a (human) subject on a bed on the basis of detection value of a load detector.

BACKGROUND ART

For the sites of medical treatment and caregiving service, it is proposed to monitor a biological state (biological condition) of a subject on the basis of such a (body weight) load of the subject on a bed as detected by load detectors. In particular, for example, it is proposed to estimate a respiratory rate of the subject on the basis of the detected load.

Patent Literature 1 discloses that the subject's respiratory rate is detected by a frequency analysis of a measuring value of load sensors arranged under legs of a bed. Patent Literature 2 discloses that load detectors are arranged under legs of a bed to find a movement of the center of gravity of a biological subject under detection on a bed and, based on the movement of the center of gravity, a respiratory motion and heartbeats of the biological subject under detection is found.

CITATION LIST

Patent Literature 1: Japanese Patent No. 4883380
Patent Literature 2: Japanese Examined Patent Publication 61-24010

SUMMARY

Technical Problem

An object of the present invention is to provide a biological state monitoring system capable of outputting an estimated value of the respiratory rate of a subject with high reliability.

Solution to the Problem

According to a first aspect of the present invention, there is provided a biological state monitoring system for monitoring a biological state of a subject on a bed, the system including:

at least one load detector configured to detect a load of the subject on the bed;

a body motion determining unit configured to determine whether or not the subject has a body motion, based on a temporal variation of a detection value of the load detector;

a respiratory rate estimating unit configured to successively obtain and output estimated values of respiratory rate of the subject, based on the temporal variation of the detection value of the load detector; and a twitch determining unit configured to determine whether or not a body motion is a twitch, based on a duration of the body motion of the subject, wherein in a case that the twitch determining unit determines that the body motion is not a twitch, the respiratory rate estimating unit ceases to output the estimated value of the respiratory rate, or outputs a first estimated value which is the latest among the estimated values obtained in a first period, the first period being directly preceding the body motion and being determined by the body motion determining unit to be a period in which the subject has no body motion, and in a case that the twitch determining unit determines that the body motion is a twitch, the respiratory rate estimating unit successively outputs newly obtained estimated values of the respiratory rate.

In the biological state monitoring system according to the first aspect, in a case that the twitch determining unit determines that the body motion is not a twitch, the respiratory rate estimating unit may output the first estimated value.

In the biological state monitoring system according to the first aspect, the twitch determining unit may determine whether or not a body motion of the subject is a twitch, based on a comparison between a predetermined threshold value and a length of a period which is determined by the body motion determining unit to be a period in which the subject has a body motion.

According to a second aspect of the present invention, there is provided a biological state monitoring system for monitoring a biological state of a subject on a bed, the system including:

at least one load detector configured to detect a load of the subject on the bed;

a body motion determining unit configured to determine whether or not the subject has a body motion, based on a temporal variation of a detection value of the load detector; and a respiratory rate estimating unit configured to successively obtain and output estimated values of respiratory rate of the subject, based on the temporal variation of the detection value of the load detector, wherein, during a period which is determined by the body motion determining unit to be a second period in which the subject has the body motion, the respiratory rate estimating unit ceases to output the estimated value of the respiratory rate, or outputs a first estimated value which is the latest among the estimated values obtained in a first period, the first period being directly preceding the second period and being determined by the body motion determining unit to be a period in which the subject has no body motion.

In the biological state monitoring system according to the second aspect, during the second period, the respiratory rate estimating unit may output the first estimated value.

The biological state monitoring system according to the first aspect or the second aspect may further include a display unit configured to display the estimated value of the respiratory rate of the subject, outputted by the respiratory rate estimating unit.

According to a third aspect of the present invention, there is provided a bed system including:

a bed; and the biological state monitoring system according to the first aspect or the second aspect.

The biological state monitoring system of the present invention is capable of outputting an estimated value of the respiratory rate of a subject with high reliability.

DESCRIPTION OF EMBODIMENT

First Embodiment

Explanations will be made on a biological state monitoring system 100 according to a first embodiment of the present invention (FIG. 1), with an example of using the system together with a bed BD (FIG. 2) to estimate a respiratory rate of a subject S on the bed BD.

Figure 1:
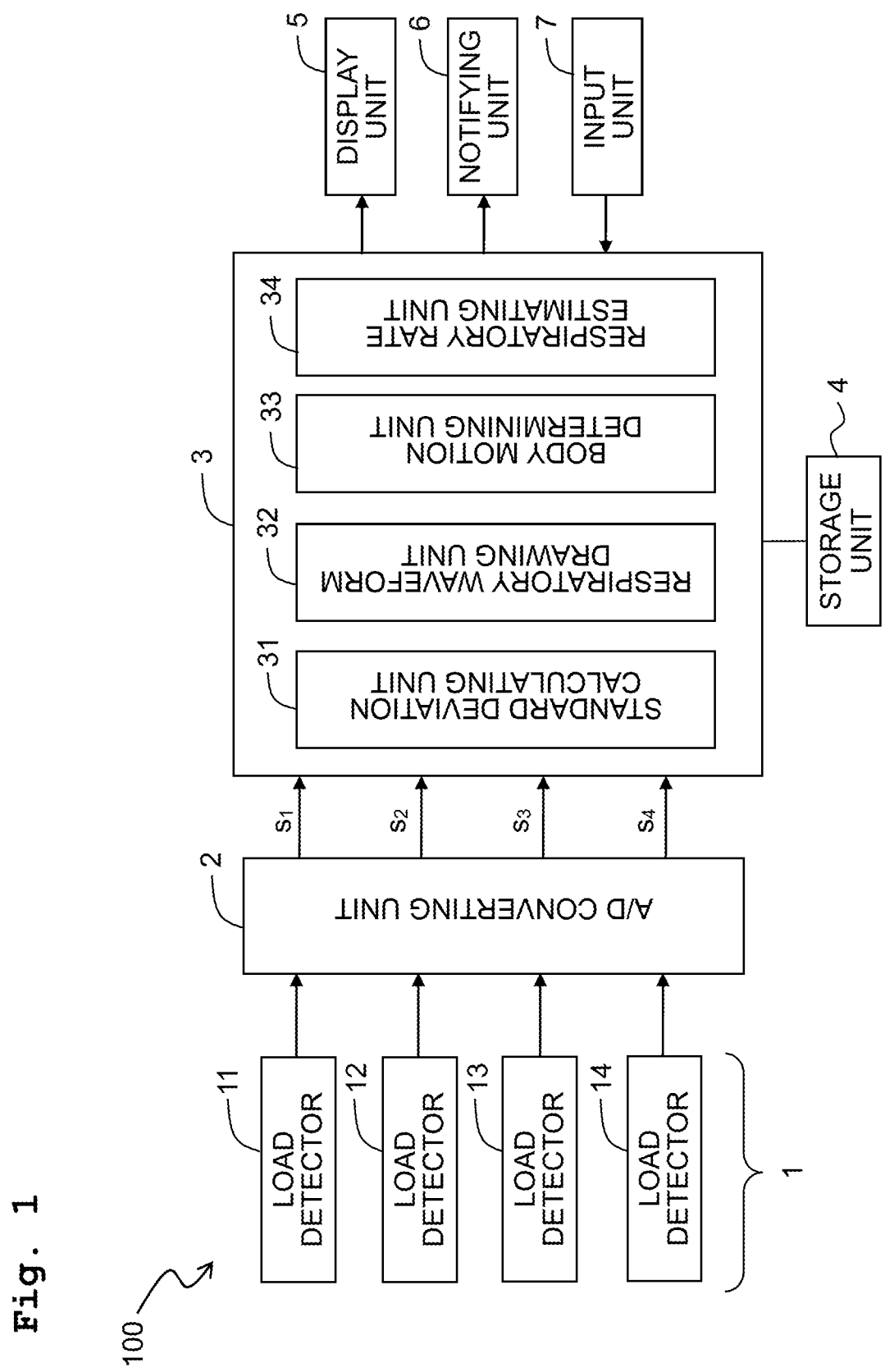
FIG. 1 is a block diagram depicting a configuration of a biological state monitoring system according to a first embodiment of the present invention.

As depicted in FIG. 1, the biological state monitoring system 100 of the first embodiment primarily has a load detecting unit 1, a control unit (controller) 3, and a storage unit 4. The load detecting unit 1 and the control unit 3 are connected via an A/D converting unit 2. The control unit 3 is further connected to a display unit 5, a notifying unit 6, and an input unit 7.

The load detecting unit 1 includes four load detectors 11, 12, 13, and 14. Each of the load detectors 11, 12, 13, and 14 is a load detector for detecting a load by using, for example, a beam-type load cell. Such a load detector is disclosed, for example, in Japanese Patent No. 4829020 and Japanese Patent No. 4002905. Each of the load detectors 11, 12, 13, and 14 is connected to the A/D converting unit 2 by way of wiring or wirelessly.

Figure 2:
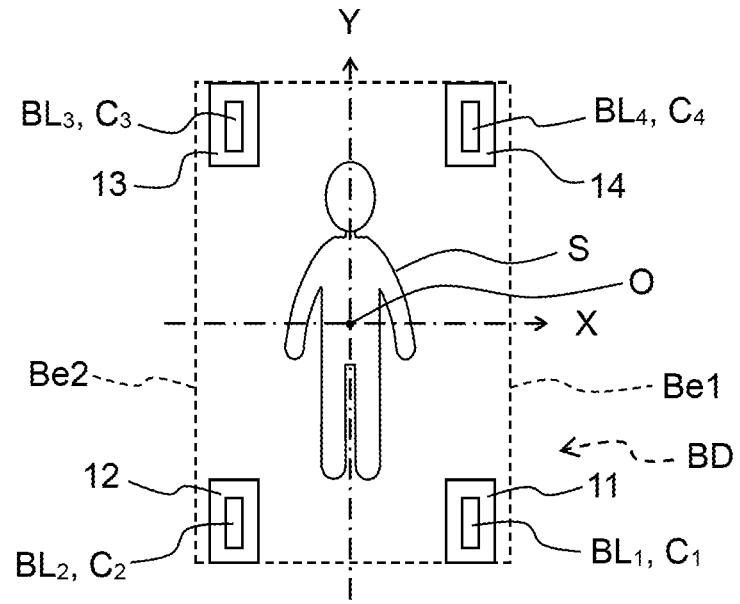
FIG. 2 is an illustrative view depicting an arrangement of load detectors for a bed.

As depicted in FIG. 2, the four load detectors 11 to 14 of the load detecting unit 1 are arranged respectively under casters $C_1$, $C_2$, $C_3$, and $C_4$ fitted on the lower ends of legs $BL_1$, $BL_2$, $BL_3$, and $BL_4$ at the four corners of the bed BD used by the subject S.

The A/D converting unit 2 includes an A/D convertor connected respectively to the load detecting unit 1 and the control unit 3 by way of wiring or wirelessly, to convert analog signals fed from the load detecting unit 1 to digital signals.

The control unit 3 is a dedicated or general-purpose computer inside which a standard deviation calculating unit 31, a respiratory waveform drawing unit 32 (respiratory waveform calculating unit; respiratory waveform obtaining (acquiring) unit), a body motion determining unit 33, and a respiratory rate estimating unit (respiratory rate determining unit; respiratory rate calculating unit) are constructed.

The storage unit 4 is a storage device for storing data used in the biological state monitoring system 100 and, for example, a hard disk (magnetic disk) can be used for that purpose.

The display unit 5 is monitor such as a liquid crystal monitor or the like for displaying information outputted from the control unit 3 to users of the biological state monitoring system 100.

The notifying unit 6 includes a device to auditorily perform a predetermined notification on the basis of the information fed from the control unit 3, such as a speaker, for example.

The input unit 7 is an interface for performing predetermined inputs for the control unit 3, which may be a keyboard and a mouse.

An explanation will be made on an operation of estimating (determining) the respiratory rate of the subject on the bed by using the biological state monitoring system 100 of such kind.

Figure 3:
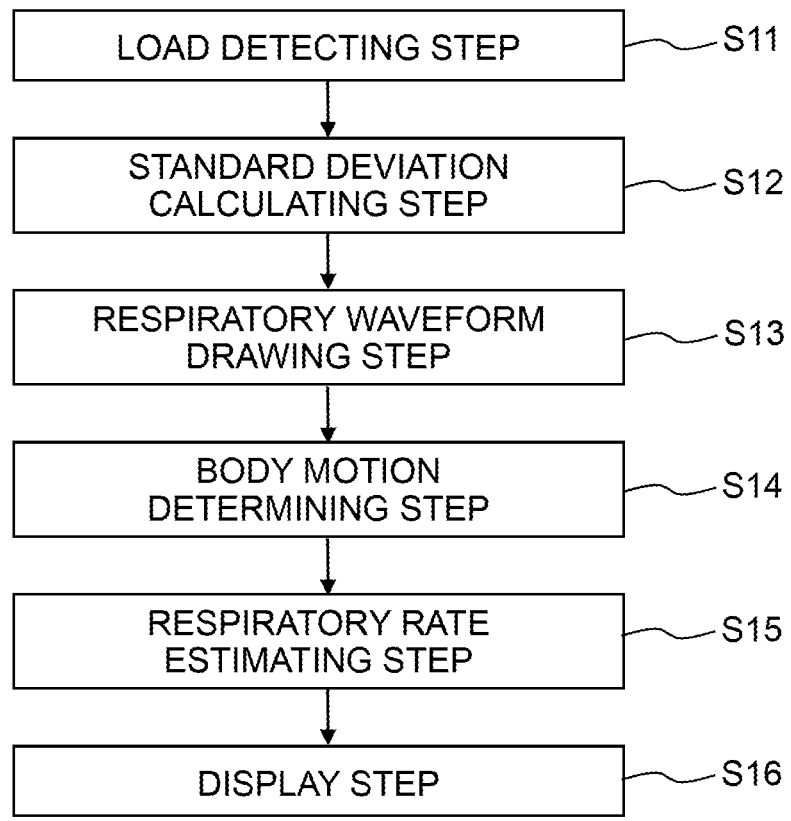
FIG. 3 is a flow chart depicting a method for estimating a respiratory rate by using the biological state monitoring system of the first embodiment of the present invention.

As depicted in the flow chart of FIG. 3, estimation of the respiratory rate of the subject performed by using the biological state monitoring system 100 includes a load detecting step S11 for detecting the load of a subject S, a standard deviation calculating step S12 for calculating a standard deviation showing the degree of variation of the detected load, a respiratory waveform drawing step S13 for drawing a respiratory waveform of the subject on the basis of the detected load, a body motion determining step S14 for determining the body motion of the subject by using the standard deviation found in the standard deviation calculating step S12, and the amplitude of the respiratory waveform drawn in the respiratory waveform drawing step S13, a respiratory rate estimating step S15 for estimating and outputting the respiratory rate of the subject on the basis of the respiratory waveform drawn in the respiratory waveform drawing step S13, and a display step S16 for displaying the outputted respiratory rate.

[The Load Detecting Step]

In the load detecting step S11, the load detectors 11, 12, 13, and 14 are used to detect the load of the subject S on the bed BD. The load of the subject S on the bed BD is applied dispersively to the load detectors 11 to 14 arranged respectively under the legs $BL_1$ to $BL_4$ of the bed BD at the four corners. The load of the subject S is detected dispersively by the four load detectors.

Each of the load detectors 11 to 14 detects the load (or variation of load), and outputs the result as an analog signal to the A/D converting unit 2. The A/D converting unit 2 converts the analog signal into a digital signal through a sampling period of 5 milliseconds, for example, and then outputs the digital signal (to be referred to below as "load signal") to the control unit 3. Hereinafter, the term "load signals $s_1$, $s_2$, $s_3$, and $s_4$" will be used to refer respectively to the load signals obtained in the A/D converting unit 2 by converting the analog signals outputted from the load detectors 11, 12, 13, and 14 into the digital format.

[The Standard Deviation Calculating Step]

In the standard deviation calculating step S12, the standard deviation calculating unit 31 calculates standard deviations $\sigma_1$, $\sigma_2$, $\sigma_3$, and $\sigma_4$ (moving standard deviations) of a sampling value included in a predetermined sampling period (5 seconds for example) for each of load signals $s_1$, $s_2$, $s_3$, and $s_4$. The calculation may be performed at any time (or continuously), with the sampling period of, for example, past 5 seconds.

Figure 4:
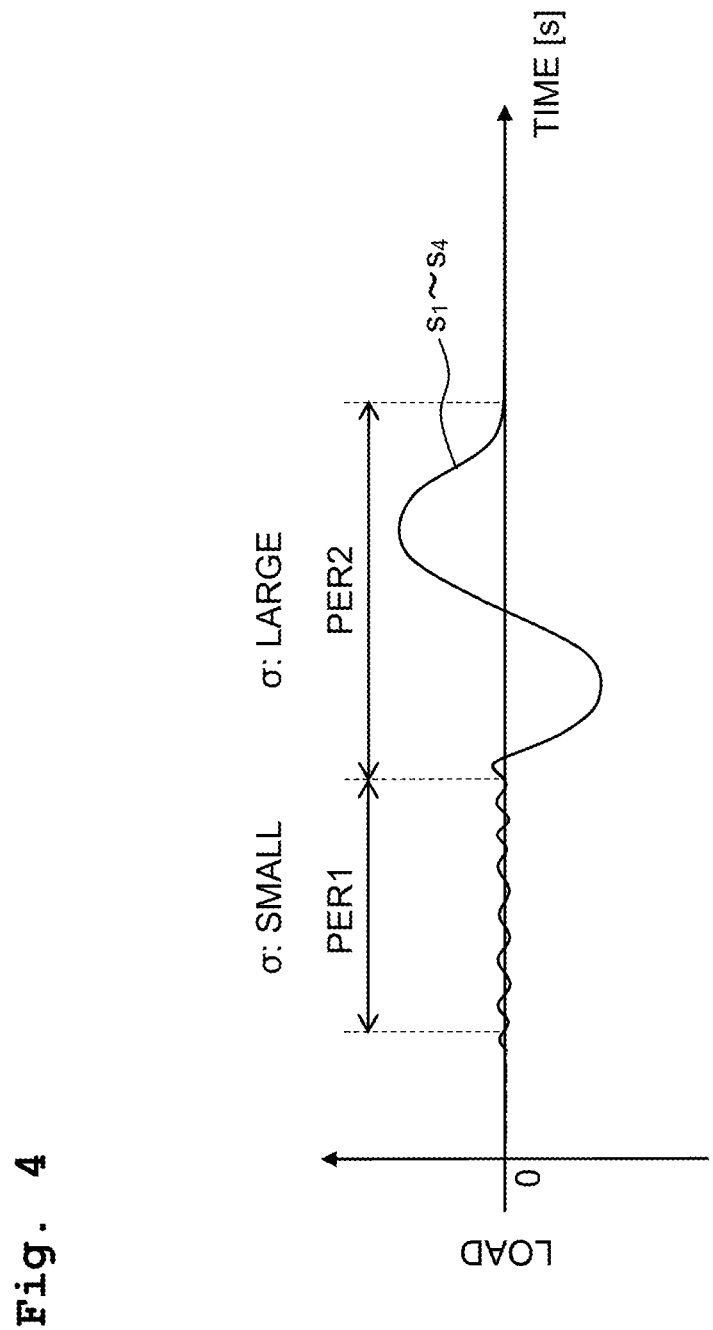
FIG. 4 is a schematic graph depicting an aspect of variation in load values detected by the load detectors in both a resting period when a subject only respires and a body motion period when the subject is performing a body motion.

The standard deviation denotes the magnitude of variation (dispersion) of the sampling value. Thus, as depicted in FIG. 4, the standard deviations $\sigma_1$ to $\sigma_4$ become small during a period PER1 in which the subject S is resting on the bed BD and there is a small magnitude of variation in the load signals $s_1$ to $s_4$. On the other hand, the standard deviations $\sigma_1$ to $\sigma_4$ become large during a period PER2 in which the subject S is moving his/her body (in which there is a body motion arising in the subject S) and there is a large magnitude of variation in the load signals $s_1$ to $s_4$.

Therefore, during a period when there is a body motion arising in the subject S, the standard deviations $\sigma_1$ to $\sigma_4$ have larger values in comparison to a period when there is no body motion arising in the subject S.

In the present specification and in the present invention, the term "body motion" refers to any motion of the subject's head, torso (trunk, body-trunk), and/or four limbs. The body motion does not include motions of internal organs, blood vessels and the like along with the respirations, heartbeats, and the like. As an example, the body motion can be classified into a large body motion along with the motion of the subject S in the torso (trunk, body-trunk), and a small body motion along with the motion of the subject only in the four limbs, the head, and/or the like. One example of the large body motion is turn-over, sit-up or get-up, or the like, whereas one example of the small body motion is, a motion of the hands, the feet, the head or the like during sleep. When heartbeats, respirations and body motions arise in the subject, the load signals $s_1$ to $s_4$ fed from the load detectors 11 to 14 vary accordingly. The magnitude of variation increases in the order of the variation due to the heartbeats of the subject S, the variation due to the respirations of the subject S, the variation due to the small body motion of the subject S, and the variation due to the large body motion of the subject S.

Note that in the determination of a body motion of the subject described in the present specification and in the present invention, the magnitude of variation in the load signals $s_1$ to $s_4$ due to the heartbeats of the subject S is so small as neglectable. Therefore, in the present specification and in the present invention, the term "the subject only (merely) respires (or the subject merely performs a respiration)", the load values and the load signals "vary due only to the respiration(s)", and the like are used to mean that the subject has no body motion, and the load values and the load signals show no variation due to the body motion, but not to mean that the subject does not have heartbeats, the load values and the load signals do not include the variation due to the heartbeats, etc.

[The Respiratory Waveform Drawing Step]

In the respiratory waveform drawing step S13, the respiratory waveform drawing unit 32 (respiratory waveform calculating unit; respiratory waveform obtaining (acquiring) unit) draws a respiratory waveform of the subject S on the basis of the load signals $s_1$ to $s_4$.

The respiration of human is performed by moving the chest and the diaphragm to expand and shrink the lungs. In this context, when the air is inhaled (or an inspiration is performed), i.e., when the lungs are expanded, the diaphragm is lowered downwardly, and the internal organs are also moved downwardly. On the other hand, when the air is expired (or an expiration is performed), i.e., when the lungs are shrunk, the diaphragm is raised upwardly, and the internal organs are also moved upwardly. As disclosed in the specification of Japanese Patent No. 6105703 granted to the present applicant, the center of gravity G (of the subject) moves slightly along with the movement of the internal organs, the moving direction thereof being approximately along the subject's backbone extending direction (body axis direction).

In the present specification and in the present invention, the term "respiratory waveform (respiration waveform)" refers to a waveform showing an aspect of the oscillation (vibration) of the subject's center of gravity oscillating (vibrating) in the subject's body axis direction due to the subject's respirations, by plotting the aspect on the temporal axis. One period of the respiratory waveform corresponds to one respiration of the subject (one inspiration and expiration). The amplitude of the respiratory waveform is affected by the subject's (physical) frame (build, physique) and/or respiratory depth. In particular, for example, if the subject has a large frame or the subject performs a deep respiration, then the amplitude becomes large, whereas if the subject has a small frame or the subject performs a shallow respiration, then the amplitude becomes small.

The respiratory waveform drawing unit 32 draws, in particular, the respiratory waveform in the following manner.

Figure 5:
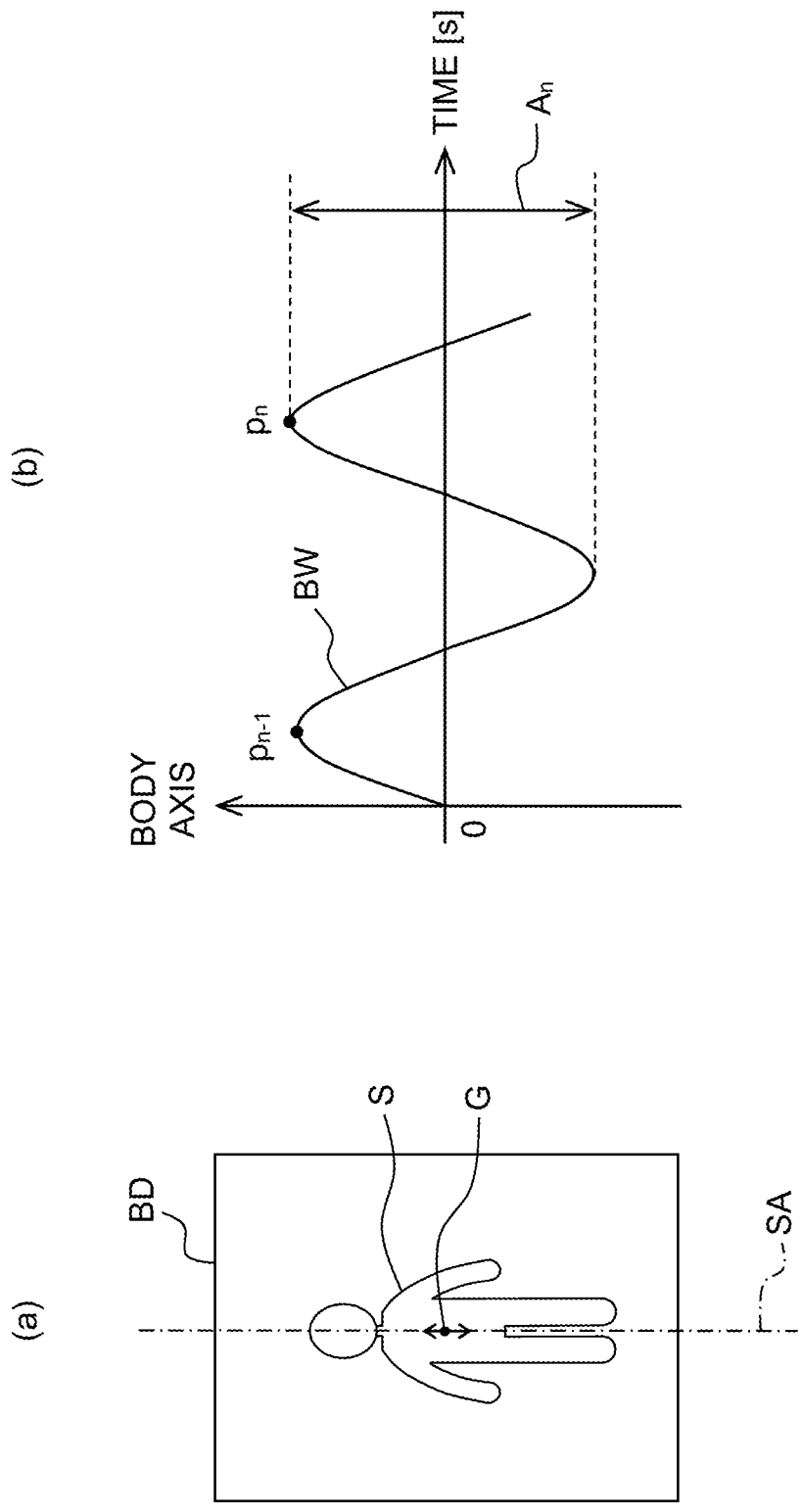
FIG. 5(a) is an illustrative view conceptionally depicting an aspect where the center of gravity of the subject oscillates or vibrates in a body axis direction of the subject according to the respirations of the subject.
FIG. 5(b) is a graph depicting an example of a respiratory waveform drawn on the basis of the oscillation of the center of gravity of the subject according to the respirations of the subject.

First, the respiratory waveform drawing unit 32 calculates the position of the center of gravity G of the subject S at each sampling time on the basis of the load signals $s_1$ to $s_4$ fed from the load detecting unit 1. As depicted in FIG. 5(a), the center of gravity G of the subject S oscillates in the direction of the body axis SA of the subject S in accordance with or due to the respiration of the subject S.

Next, the respiratory waveform drawing unit 32 draws a respiratory waveform BW (FIG. 5(b)) by way of plotting, on the vertical axis of a graph, the distance between the positions obtained by projecting the position of the center of gravity G at each time on the body axis SA, and the oscillation center of oscillation of the center of gravity G according to the respiration. The direction of the vertical axis of the graph matches the direction of the body axis SA. The horizontal axis of the graph shows time.

Note that it is not necessary for the respiratory waveform drawing unit 32 to actually draw the respiratory waveform but it is possible to only obtain data indicating the respiratory waveform.

[The Body Motion Determining Step]

In the body motion determining step S14, the body motion determining unit 33 uses the standard deviations $\sigma_1$ to $\sigma_4$ calculated in the standard deviation calculating step S12 and the amplitude of the respiratory waveform BW drawn in the respiratory waveform drawing step S13, to determine whether or not there is a body motion arising in the subject S (whether or not the subject S has a body motion).

The determination is performed in the following manner in particular for example.

First, the body motion determining unit 33 detects the peaks for the respiratory waveform BW drawn in the respiratory waveform drawing step S13, and calculates the difference between the minimum value over the period between the latest peak $p_n$ and the previous peak $p_{n-1}$, and the latest peak $p_n$, as the latest amplitude $A_n$ of the respiratory waveform BW (FIG. 5(b)). Then, the body motion determining unit 33 finds an average amplitude $A_{Avn}$ which is a simple average (value) of the amplitude $A_n$ and the amplitudes $A_{n-1}$, $A_{n-2}$, . . . which are calculated before the amplitude $A_n$. While an arbitrary number of amplitudes $A_n$ can be used for calculating the average amplitude $A_{Avn}$, as one example, the number may be such as obtained in a sampling period of 5 seconds or so.

Note that in order to confirm that the respiratory waveform BW, which is involved in calculating the amplitudes $A_n$, $A_{n-1}$, $A_{n-2}$, . . . and the average amplitude $A_{AVn}$, is the respiratory waveform obtained from a resting period (during which the subject only respires (performs respirations) without body motion arising), (i.e., in order to confirm that there is no error included due to the movement of the center of gravity because of some body motion), a comparison may be made between a threshold value $\sigma_0$ and either a simple average $\sigma_{AV}$ of the standard deviations $\sigma_1$ to $\sigma_4$ or any one of the standard deviations $\sigma_1$ to $\sigma_4$. The threshold value $\sigma_0$ is set at such a small value as able to reliably determine that there is no body motion arising in the subject S as long as the simple average $\sigma_{AV}$ or any one of the standard deviations $\sigma_1$ to $\sigma_4$ is smaller than that value (conversely, even if the simple average $\sigma_{AV}$ or any one of the standard deviations $\sigma_1$ to $\sigma_4$ is not smaller than that value, it is still possible that there is no body motion arising in the subject S).

Next, the body motion determining unit 33 finds normalized standard deviations $\sigma s_1$ to $\sigma s_4$ by the following Formula (Equation) 1.

$$\sigma s_m = \sigma_m / A_{AVn} \ (m=1,2,3,4) \quad \text{(Formula 1)}$$

Then, the body motion determining unit 33 finds a simple average $\sigma s_{AV}$ of the calculated normalized standard deviations $\sigma s_1$ to $\sigma s_4$ and, based on a comparison between the simple average $\sigma s_{AV}$ and a predetermined threshold value $\sigma s_{TH}$, determines whether or not there is a body motion arising in the subject S (whether or not the subject S has a body motion). In particular, for example, if the simple average $\sigma s_{AV}$ is larger than or equal to the threshold value $\sigma s_{TH}$, then it is determined that there is a body motion arising in the subject S (the subject S has a body motion), whereas if the simple average $\sigma s_{AV}$ is smaller than the threshold value $\sigma s_{TH}$, then it is determined that there is no body motion arising in the subject S (the subject S has no body motion).

During a period when it is determined that there is no body motion arising in the subject S, the body motion determining unit 33 calculates the latest amplitude $A_n$ for each one period of the respiratory waveform BW on the basis of the respiratory waveform BW acquired by the respiratory waveform drawing unit 32. Then, using the average amplitude $A_{AVn}$ calculated anew by using the value of the calculated latest amplitude $A_n$, and the values of the standard deviations $\sigma_1$ to $\sigma_4$ calculated at each sampling time (as an example, every 5 milliseconds), the body motion determining unit 33 calculates, successively, the normalized standard deviations $\sigma s_1$ to $\sigma s_4$ by the Formula 1 and calculates the simple average $\sigma s_{AV}$.

Determining whether or not there is a body motion arising in the subject S is performed by the successive comparisons between the predetermined threshold value $\sigma s_{TH}$ and the simple average $\sigma s_{AV}$ calculated successively in the above manner.

After it is determined as a result of the determination that there is a body motion arising in the subject S, the body motion determining unit 33 ceases to update the average amplitude $A_{AVn}$ and continues to calculate the simple average $\sigma s_{AV}$ using the average amplitude $A_{AVn}$ having been calculated by this point. Then, based on a comparison between the calculated simple average $\sigma s_{AV}$ and the threshold value $\sigma s_{TH}$, the body motion determining unit 33 continues to determine whether or not there is a body motion arising in the subject S. This is because during a period when there is a body motion arising in the subject S, the amplitude and period of the respiratory waveform BW vary greatly due to the influence of the body motion, and thereby it is difficult to calculate a new amplitude $A_n$ and the average amplitude $A_{AVn}$ without error.

Next, if it is determined again that there is no body motion arising in the subject S, then based on the respiratory waveform BW acquired by the respiratory waveform drawing unit 32, the body motion determining unit 33 calculates the value of the latest amplitude $A_n$ and, using the same, calculates the average amplitude $A_{AVn}$ anew. Then, the body motion determining unit 33 calculates the simple average $\sigma s_{AV}$ using the latest average amplitude $A_{AVn}$ and, based on a comparison between the calculated simple average $\sigma s_{AV}$ and the predetermined threshold value $\sigma s_{TH}$, the body motion determining unit 33 continues to determine whether or not there is a body motion arising in the subject S.

Figure 6:
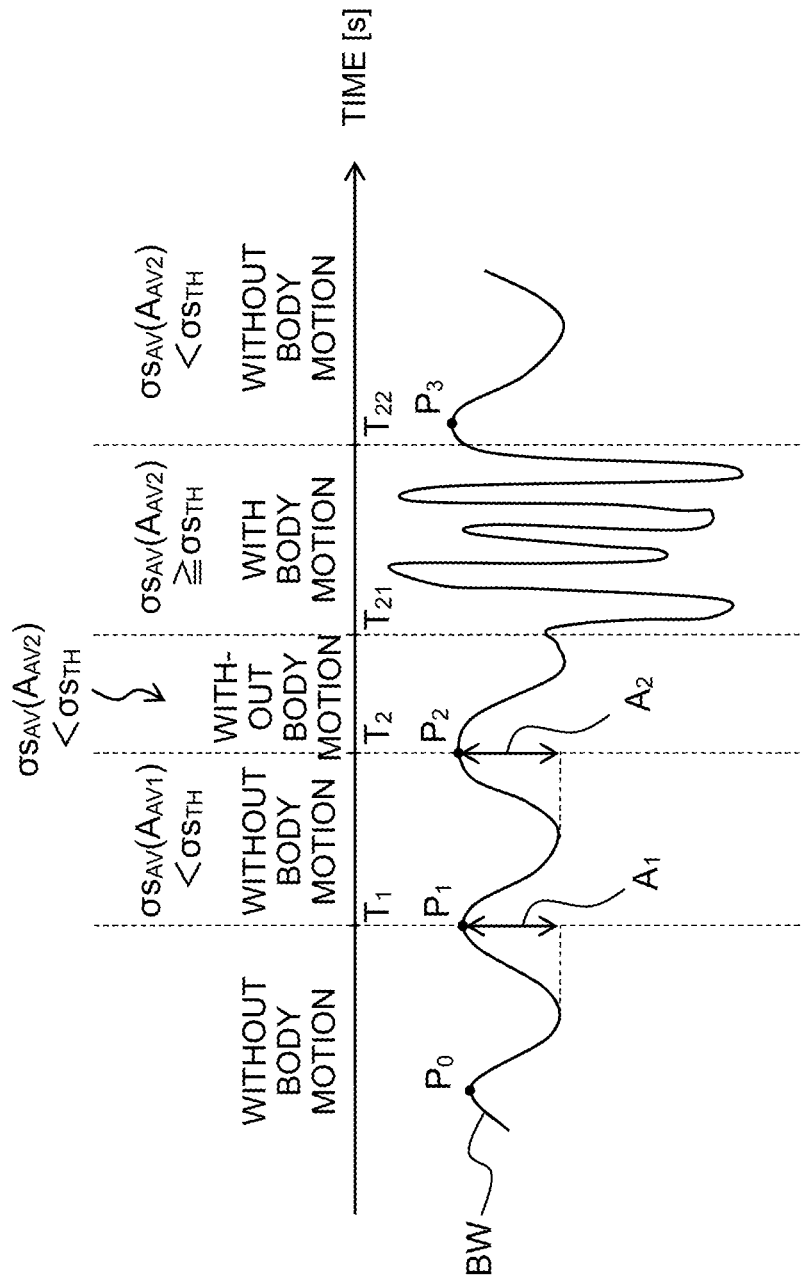
FIG. 6 is an illustrative view for explaining an example of specific method for determining the body motion with a body motion determining unit.

Referring to FIG. 6, a particular example of this step will be explained.

As depicted in FIG. 6, if a peak $P_1$ of the respiratory waveform BW and the latest amplitude $A_1$ are obtained at the time $T_1$, then for the period from the time $T_1$, the body motion determining unit 33 uses the average amplitude $A_{AVn}$ which is the simple average of the amplitude $A_1$ and the amplitudes $A_0$, $A_{-1}$, . . . (all not shown) obtained right therebefore, to calculate successively the normalized standard deviations $\sigma s_1$ to $\sigma s_4$ and the simple average $\sigma s_{AV}$ (to be referred to here as $\sigma s_{AV}(A_{AV1})$); and determines whether or not there is a body motion arising in the subject S, based on a comparison between the simple average $\sigma s_{AV}(A_{AV1})$ and the threshold value $\sigma s_{TH}$.

Next, if another peak $P_2$ of the respiratory waveform BW and the latest amplitude $A_2$ are obtained at the time $T_2$, then for the period from the time $T_2$, the body motion determining unit 33 uses the average amplitude $A_{AV2}$ calculated by using the amplitude $A_2$, to calculate successively the normalized standard deviations $\sigma s_1$ to $\sigma s_4$ and the simple average $\sigma s_{AV}$ (to be referred to here as $\sigma s_{AV}(A_{AV2})$); and determines whether or not there is a body motion arising in the subject S, based on the comparison between the simple average $\sigma s_{AV}(A_{AV2})$ and the threshold value $\sigma s_{TH}$.

At the time $T_{21}$, if there is a body motion arising in the subject S, then the body motion determining unit 33 determines that there is a body motion arising in the subject S on the basis of the simple average $\sigma s_{AV}(A_{AV2})$ being equal to or larger than the threshold value $\sigma s_{TH}$. Then, after that, for the period when the simple average $\sigma s_{AV}(A_{AV2})$ is equal to or larger than the threshold value $\sigma s_{TH}$, the body motion determining unit 33 continues to determine the body motion using the simple average $\sigma s_{AV}(A_{AV2})$.

At the time $T_{22}$, if the body motion has come to an end in the subject S, then the body motion determining unit 33 determines that there is no body motion arising in the subject S on the basis of the simple average $\sigma s_{AV}$ ($A_{AV2}$) being smaller than the threshold value $\sigma s_{TH}$. After that, the body motion determining unit 33 continues to determine the body motion using the simple average $\sigma s_{AV}$ ($A_{AV2}$) until the latest amplitude $A_n$ of the respiratory waveform BW is obtained and the latest average amplitude $A_{AVn}$ is calculated again.

The body motion determining unit 33 uses the amplitude $A_n$ (average amplitude $A_{AVn}$) of the respiratory waveform to normalize the values of the standard deviations $\sigma_1$ to $\sigma_4$. The reason therefor is as follows.

As described above, generally speaking, the values of the standard deviations $\sigma_1$ to $\sigma_4$ become larger during a period when there is a body motion arising in the subject S. Therefore, it is conceivable to determine whether or not there is a body motion arising in the subject S by way of comparison between the values of the standard deviations $\sigma_1$ to $\sigma_4$ and a predetermined threshold value.

However, according to the discovery and knowledge of the present inventors, for a subject who has a large frame, the values of the standard deviations $\sigma_1$ to $\sigma_4$ may still be comparatively large even during a period of only performing respirations without the body motion because the movement of his/her internal organs due to the respirations is also large. Further, even for a subject who does not have a large frame, the values may still become large if, for example, the subject performs a deep respiration. Hence, if the body motion determination is performed by comparing the values of the standard deviations $\sigma_1$ to $\sigma_4$ to a predetermined threshold value, in such a case, even though there is no body motion arising in the subject, a mistaken determination may be made to give the incorrect result that there is a body motion arising in the subject.

On the other hand, if the respiratory waveform is focused on, then as described earlier on, the amplitude of the respiratory waveform is affected by the subject's frame and/or respiratory depth; therefore, if the subject has a large frame or the subject performs a deep respiration, then the amplitude becomes large, whereas if the subject has a small frame or the subject performs a shallow respiration, then the amplitude becomes small.

That is, by dividing the values of the standard deviations $\sigma_1$ to $\sigma_4$ by the average amplitude $A_{AVn}$ of the respiratory waveform BW to perform the normalization, it is possible to reduce (compensate; correct) the influence on the values of the standard deviations $\sigma_1$ to $\sigma_4$, exerted by the subject's frame and/or respiratory depth. Then, by using the normalized standard deviations $\sigma s_1$ to $\sigma s_4$ obtained through such normalization to determine the body motion, it is possible to raise the precision of determining the body motion.

[The Respiratory Rate Estimating Step]

In the respiratory rate estimating step S15, the respiratory rate estimating unit 34 (the respiratory rate determining unit) estimates (determines) the respiratory rate of the subject S on the basis of the respiratory waveform BW of the subject S drawn in the respiratory waveform drawing step S13, and outputs the estimated (determined) respiratory rate to the display unit 5.

In particular, the respiratory rate estimating unit 34 estimates the respiratory rate on the basis of the respiratory waveform BW by the following method.

The respiratory rate estimating unit 34 detects peaks in predetermined periods for the respiratory waveform BW drawn in the respiratory waveform drawing step S13. Then, when a new peak is detected, the respiratory rate estimating unit 34 finds distances (to be referred to below as inter-peak distances t) between any two adjacent peaks of the plurality of peaks included between a first time point at which the new peak is detected and a second time point before (preceding) the first time point by a predetermined time period (25 seconds for example; to be referred to below as "sampling time period for estimation" as appropriate).

Figure 7:
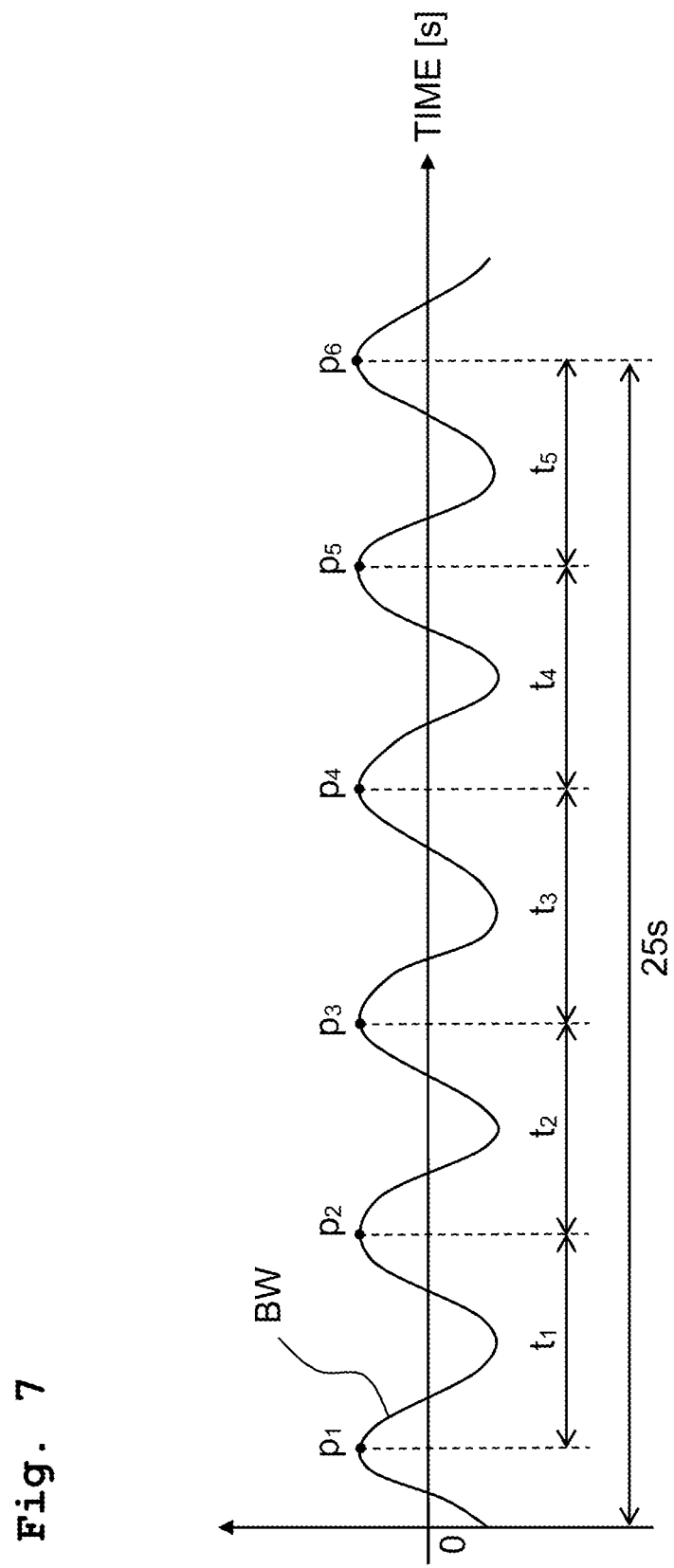
FIG. 7 is an illustrative view for explaining an exemplary method for estimating the respiratory rate of the subject on the basis of the respiratory waveform.

FIG. 7 depicts one example of the respiratory waveform BW included in the sampling time period for estimation over 25 seconds with peaks $p_1$ to $p_6$ of the respiratory waveform BW, and inter-peak distances $t_1$ to $t_5$ between the peaks $p_1$ to $p_6$.

Next, the respiratory rate estimating unit 34 finds an average value $t_{AV}$ of the plurality of inter-peak distances t by the following Formula 2.

$$t_{AV} = \frac{1}{N-1} \sum_{n=1}^{N-1} t_n \qquad \text{(Formula 2)}$$

Herein, N is the number of peaks of the respiratory waveform BW included in the sampling time period for estimation. The average value $t_{AV}$ approximately corresponds to the average value of the respiratory periods of the subject S during the sampling time period for estimation.

Thereafter, the respiratory rate estimating unit 34 calculates an estimated value R of the respiratory rate over one minute of the subject S by the following Formula 3. Then, the calculated estimated value R is outputted to the display unit 5 as the estimated respiratory rate.

$$R = 60/t_{AV} \qquad \text{(Formula 3)}$$

Further, the respiratory rate estimating unit 34 of this embodiment adjusts the value of the respiratory rate for output according to whether or not the subject S has a body motion. This adjustment will be explained as follows.

The respiratory rate estimating unit 34 successively calculates the estimated value R of the respiratory rate by using the Formulas 2 and 3 according to the above method whenever a peak of the respiratory waveform BW is detected both in a period (resting period) when the body motion determining unit 33 determines that the subject S does not have a body motion and in a period (body motion period) when the body motion determining unit 33 determines that the subject S has a body motion.

Then, in the resting period (excluding a predetermined period after the transition (shifting) from the body motion period to the resting period, as will be described later on), the calculated estimated values R are outputted successively to the display unit 5 as the estimated respiratory rates.

On the other hand, in the body motion period, the respiratory rate estimating unit 34 outputs the estimated value (first estimated value) R calculated right before the transition (shifting) from the resting period to the body motion period, that is, the estimated value R calculated last in the resting period right therebefore, instead of the estimated value R of the respiratory rate calculated successively by using the Formulas 2 and 3 according to the above method, to the display unit 5 as the estimated respiratory rate.

Further, when a transition from a first resting period to a body motion period occurred and then a transition from the body motion period to a second resting period occurred, in a predetermined period after the transition from the body motion period to the second resting period, the respiratory rate estimating unit 34 outputs the value outputted in the preceding body motion period, that is, the estimated value R calculated right before the transition from the first resting period to the body motion period, to the display unit 5 as the estimated respiratory rate, instead of the estimated value R of the respiratory rate calculated successively by using the Formulas 2 and 3 according to the above method.

Then, after detecting two peaks of the respiratory waveform BW in the second resting period, the respiratory rate estimating unit 34 finds (obtains) the inter-peak distance t between those two peaks, and uses the value of the inter-peak distance t as the value of the average value $t_{AV}$ to calculate the estimated value R of the respiratory rate by the Formula 3. Then, the respiratory rate estimating unit 34 outputs the estimated value R calculated anew to the display unit 5 as the estimated respiratory rate, instead of the value outputted fixedly in the body motion period and the following predetermined period, that is, the estimated value R calculated right before the transition from the first resting period to the body motion period.

In the same manner, at the time points at which three and four peaks of the respiratory waveform BW have been detected, the respiratory rate estimating unit 34 obtains the inter-peak distances t between two adjacent peaks of the three and four peaks, respectively, to calculate the estimated value R of the respiratory rate by the Formula 3 by using a simple average (value) of those obtained inter-peak distances t as the value of the average value $t_{AV}$. Then, the respiratory rate estimating unit 34 outputs the calculated values as the estimated respiratory rate to the display unit 5. Then, after the sampling time period for estimation (25 seconds for here) has elapsed after (since) the transition from the body motion period to the second resting period, the respiratory rate estimating unit 34 restarts calculating the average value $t_{AV}$ by using the above Formula 2 to calculate the estimated value R by applying the calculated average value $t_{AV}$ to the above Formula 3, and output the calculated value to the display unit 5 as the estimated respiratory rate.

A specific example of this step will be explained, using FIG. 8.

Figure 8:
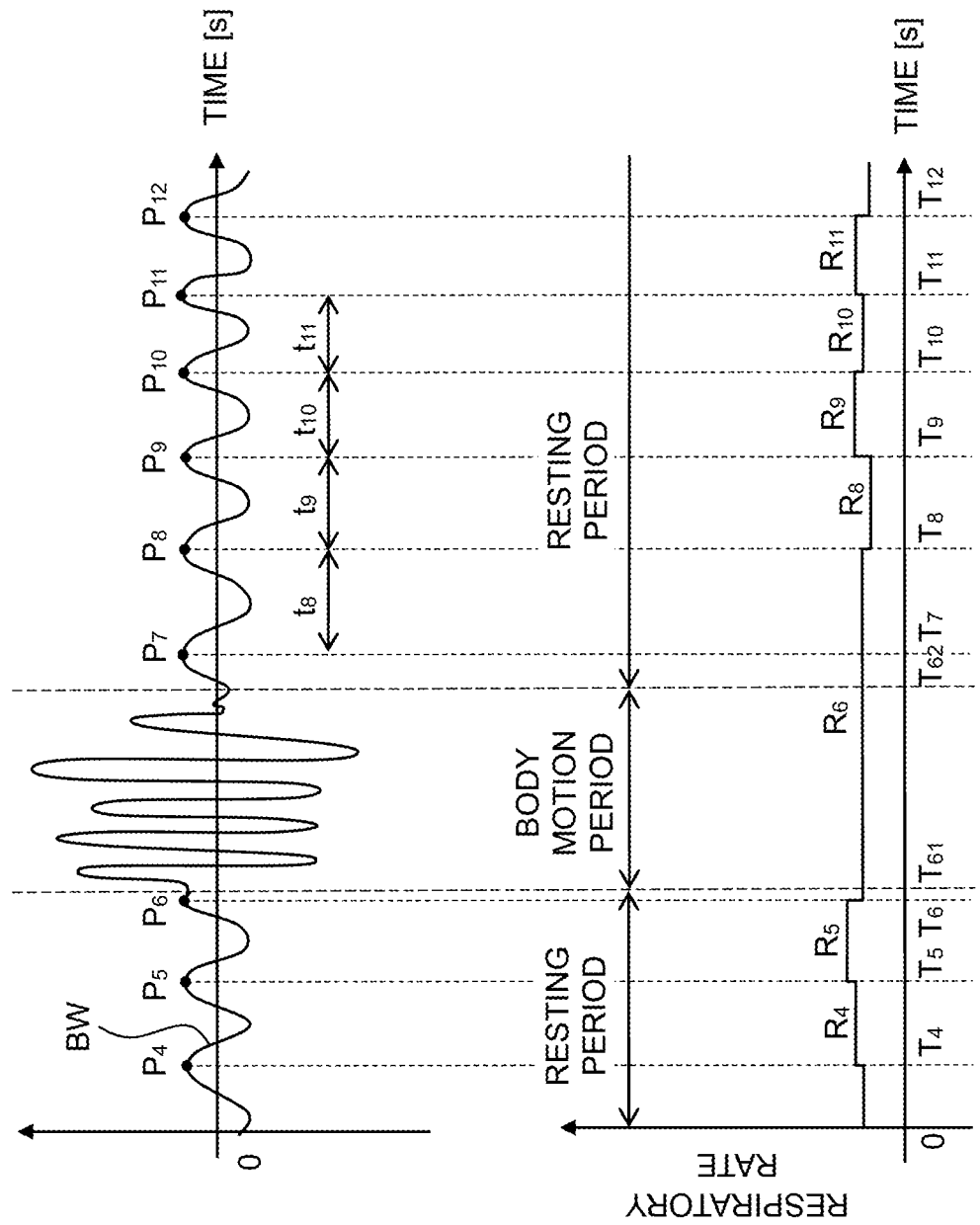
FIG. 8 is an illustrative view for explaining a specific example of a respiratory rate estimating step performed by a respiratory rate estimating unit.

As depicted in FIG. 8, after detecting the peak $P_4$ of the respiratory waveform BW at the time $T_4$ included in the resting period, the respiratory rate estimating unit 34 calculates the estimated value R of the respiratory rate by the above Formulas 2 and 3, on the basis of the respiratory waveform BW found in the sampling time period for estimation over 25 seconds with the time $T_4$ as the terminal, and outputs the calculated value as the estimated respiratory rate. Here, suppose that the respiratory rate $R_4$ is outputted. In the same manner, after detecting the peaks $P_5$ and $P_6$ of the respiratory waveform BW at the times $T_5$ and $T_6$, the respiratory rate estimating unit 34 calculates the estimated values R of the respiratory rate by the above Formulas 2 and 3, on the basis of the respiratory waveform BW found in the sampling time period for estimation with the times $T_5$ and $T_6$ as the terminals, and outputs the calculated values as the estimated respiratory rates. Here, suppose that the respiratory rates $R_5$ and $R_6$ are outputted.

Next, if a body motion arises in the subject S at the time $T_{61}$, then the respiratory rate estimating unit 34 switches the estimated value of the respiratory rate for output from the estimated value R calculated anew by using the above Formulas 2 and 3 to the estimated value calculated right before the time $T_{61}$ (equal to the respiratory rate $R_6$), on the basis of the body motion determining unit 33 having determined that the subject S has a body motion. Then, during the period when the body motion determining unit 33 determines that the body motion is arising in the subject S (the subject S has the body motion), that is, during the body motion period, the respiratory rate estimating unit 34 keeps outputting the respiratory rate $R_6$ as the estimated respiratory rate.

Further, after the body motion of the subject S comes to an end at the time $T_{62}$ such that the body motion determining unit 33 determines that there is no body motion arising in the subject S (that is, after returning to a resting period), the respiratory rate estimating unit 34 also keeps outputting the estimated value calculated right before the time $T_{61}$ (equal to the respiratory rate $R_6$) as the estimated respiratory rate, through a predetermined period, instead of the estimated value R calculated anew by using the above Formulas 2 and 3.

Then, after detecting the second peak $P_8$ after the body motion of the subject S comes to an end at the time $T_8$, the respiratory rate estimating unit 34 finds the inter-peak distance $t_8$ between the first peak $P_7$ and the peak $P_8$ after the body motion of the subject S comes to the end. Then, using the inter-peak distance $t_8$ as the average value $t_{AV}$, the respiratory rate estimating unit 34 calculates the estimated value R of the respiratory rate by the Formula 3, and outputs the newly calculated estimated value R as the estimated respiratory rate instead of the value outputted fixedly after the time $T_{61}$ (the respiratory rate $R_6$). Here, suppose that the respiratory rate $R_8$ is outputted.

After detecting the third peak $P_9$ after the body motion of the subject S comes to an end at the time $T_9$, the respiratory rate estimating unit 34 finds the inter-peak distance $t_9$ between the second peak $P_8$ and the peak $P_9$ after the body motion of the subject S comes to the end. Then, using a simple average of the inter-peak distance $t_8$ and the inter-peak distance $t_9$ as the average value $t_{AV}$, the respiratory rate estimating unit 34 calculates the estimated value R of the respiratory rate by the Formula 3, and outputs the calculated value as the estimated respiratory rate. Here, suppose that the respiratory rate $R_9$ is outputted.

In the same manner, after detecting the fourth peak $P_{10}$ and the fifth peak $P_{11}$ after the body motion of the subject S comes to an end at the times $T_{10}$ and $T_{11}$, the respiratory rate estimating unit 34 finds the inter-peak distance $t_{10}$ between the peak $P_9$ and the peak $P_{10}$, and the inter-peak distance $t_{11}$ between the peak $P_{10}$ and the peak $P_{11}$. Then, using the simple average of what has already been obtained in the inter-peak distances $t_8$ to $t_{11}$ as the average value $t_{AV}$, it calculates the estimated value R of the respiratory rate by the Formula 3, and outputs the calculated value as the estimated respiratory rate. Here, suppose that the respiratory rates $R_{10}$ and $R_{11}$ are outputted.

Then, after 25 seconds, which corresponds to the sampling time period for estimation, has elapsed since the time $T_{62}$, the respiratory rate estimating unit 34 restarts calculating the average value $t_{AV}$ by using the above Formula 2, to calculate the estimated value R of the respiratory rate by applying the calculated average value $t_{AV}$ to the above Formula 3. Then, it outputs the calculated value to the display unit 5 as the estimated respiratory rate.

The following statement is the reason why the respiratory rate estimating unit 34 outputs the estimated value R of the respiratory rate, calculated right before the transition from the resting period to the body motion period, as the estimated value of the respiratory rate of the subject S instead of the estimated value R calculated, in the body motion period and the predetermined initial period of the following resting period.

As depicted in FIG. 8, there are detected peaks in the respiratory waveform BW during the body motion period, too. However, as seen in the waveform depicted in FIG. 8, the respiratory waveform BW is affected and disturbed by the body motion of the subject S whereby the period of the respiratory waveform BW is also varying. Therefore, the inter-peak distances found on the basis of the peaks of the respiratory waveform BW in the body motion period do not reflect the respiratory period by their values. If the sampling time period for estimation includes a body motion period, then the average value $t_{AV}$ found by the Formula 2 is affected by the inter-peak distances which do not reflect the respiratory period in this manner. Therefore, there is also a high possibility for the estimated value R of the respiratory rate calculated by using the Formula 3 to deviate from the actual respiratory rate of the subject.

Therefore, in the body motion period and the predetermined initial period in the resting period following the body motion period, during which the body motion period is included inevitably in the sampling time period for estimation, the respiratory rate estimating unit 34 outputs the estimated value R calculated right before the transition from the resting period to the body motion period as the estimated value for those periods, instead of the estimated value R calculated anew. By virtue of this, reliability is maintained for the estimated value of the respiratory rate to offer the user of the biological state monitoring system 100.

Note that the respiratory rate estimating unit 34 may cease to detect the peaks of the respiratory waveform BW, cease to calculate the inter-peak distances, and cease to calculate the estimated values R using the Formulas 2 and 3, during the body motion period and during the predetermined period after the transition from the body motion period to the resting period.

In this embodiment, at the time point by which two peaks of the respiratory waveform BW of the resting period have been detected, the estimated value R is calculated by using the inter-peak distance between those peaks, and the calculated value is outputted. According to this method, after the transition from the body motion period to the resting period, it is possible to restart calculating and outputting the estimated value R of the respiratory rate with exclusion of the influence of disturbance of the respiratory waveform BW in the body motion period, without waiting for the passage of the time equivalent to the sampling time period for estimation. However, after an end of the body motion, it is allowable to keep outputting the estimated value R calculated right before the transition to the body motion period, until the lapse of the time almost equal to the sampling time period for estimation.

[The Display Step]

In the display step S16, the control unit 3 causes the display unit 5 to display the respiratory rate (estimated value) of the subject S outputted in the respiratory rate estimating step S15. Further, in the display step S16, the notifying unit 6 may be used to perform a notification in addition to or instead of the display using the display unit 5. In this case, for example, when the respiratory rate of the subject S reaches a predetermined set value, a notification sound may be emitted to notify the nurses, caregivers and/or others who are the users of the biological state monitoring system 100.

The effects of the biological state monitoring system 100 according to this embodiment are summarized as follows.

In a case that the subject S has a body motion, then the respiratory rate estimating unit 34 included in the biological state monitoring system 100 of this embodiment outputs the estimated value calculated right before an occurrence of the body motion, during a period in which the body motion is kept and during a predetermined period succeeding an end of the body motion, as the estimated value of the respiratory rate for those periods.

Therefore, even when the subject S has a body motion, it is possible for the biological state monitoring system 100 of this embodiment to suppress the influence of the body motion, thereby outputting the estimated value of the respiratory rate of the subject S with high reliability.

The respiratory rate estimating unit 34 included in the biological state monitoring system 100 of this embodiment restarts, at the point of detecting two peaks of the respiratory waveform BW after the transition from the body motion period to the resting period, calculating the estimated value of the respiratory rate by using the inter-peak distance between those peaks. Therefore, it is possible for the biological state monitoring system 100 of this embodiment to release the respiratory rate displayed on the display unit 5 from the state fixed at the value estimated right before a body motion, at an earlier timing after the end of the body motion.

The biological state monitoring system 100 of this embodiment uses the load detectors 11 to 14 arranged under the legs $BL_1$ to $BL_4$ of the bed BD to determine whether or not the subject S has a body motion. Therefore, it is not necessary to attach any measuring device to the body of the subject S so that the subject S will not feel discomfort and a sense of incongruity.

Second Embodiment

Next, an explanation will be made on a biological state monitoring system 200 according to a second embodiment of the present invention.

In the biological state monitoring system 100 of the above first embodiment, the respiratory rate estimating unit 34 fixes the estimated value of the respiratory rate of the subject S for output at the estimated value (the first estimated value) calculated right before a body motion period, during the body motion period and the like when a disturbance arises in the respiratory waveform due to the body motion of the subject S. In such a manner, the biological state monitoring system 100 prevents degradation of the reliability of the estimated value of the respiratory rate due to the influence of disturbance of the respiratory waveform.

In this context, it is known that a motion of muscle spasm which is called a twitch (a jerk) may occur in a person during REM sleep. Such a twitch is also a kind of body motion. The present inventors have made researches on the influence of a twitch on biological state monitoring and obtained the discovery and knowledge that even if the subject S performs a twitch, the twitch will not give rise to a large disturbance in the respiratory waveform. It is conceived that this is because the influence of the twitch which is a body motion over a short duration time (continuance time) is eliminated or reduced in the calculating process or filtering process for obtaining the respiratory waveform. On the other hand, according to the discovery and knowledge of the present inventors, even if the body motion is a twitch, the body motion determining unit still determines that a body motion has arisen.

The biological state monitoring system 200 of the second embodiment is based on the above discovery and knowledge of the present inventors, and configured not to perform estimation fixing (estimated value fixing), performed by the respiratory rate estimating unit 34 of the biological state monitoring system 100 of the first embodiment, even when the body motion determining unit determines that the subject has the body motion, provided that the body motion is a twitch. By virtue of this, the biological state monitoring system of the second embodiment can output the estimated value of the respiratory rate of the subject with even higher reliability.

Figure 9:
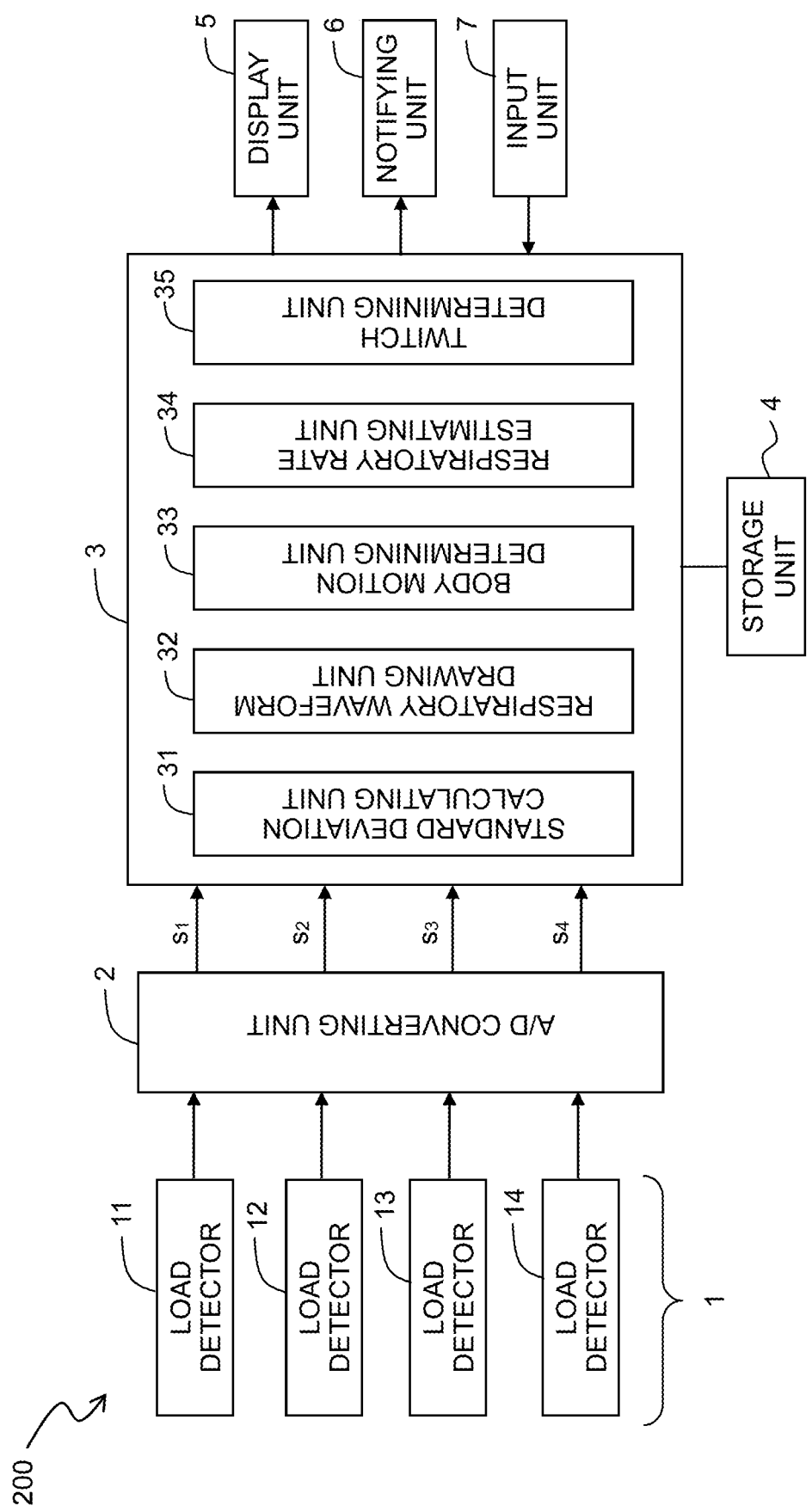
FIG. 9 is a block diagram depicting a configuration of a biological state monitoring system according to a second embodiment of the present invention.

The biological state monitoring system 200 of the second embodiment (FIG. 9) has the same configuration as the biological state monitoring system 100 of the first embodiment except for the aspect of including a twitch determining unit 35 configured to determine whether or not the body motion of the subject is a twitch. Explanation will be omitted for any configuration common to the biological state monitoring systems 100 and 200 of the first and second embodiments. How the twitch determining unit 35 operates will be described latter on.

Figure 10:
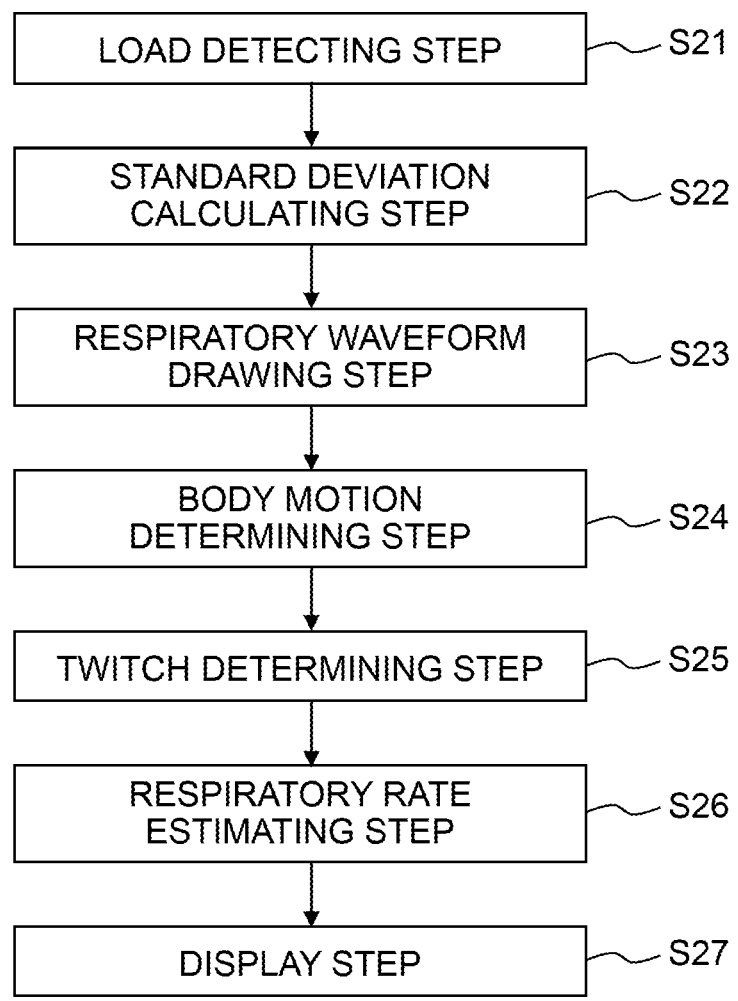
FIG. 10 is a flow chart depicting a method for estimating the respiratory rate by using the biological state monitoring system according to the second embodiment of the present invention.

As depicted in the flow chart of FIG. 10, estimation of the respiratory rate of the subject performed by using the biological state monitoring system 200 includes a load detecting step S21 for detecting the load of the subject S, a standard deviation calculating step S22 for calculating the standard deviation showing the degree of variation of the detected load, a respiratory waveform drawing step S23 for drawing the respiratory waveform of the subject on the basis of the detected load, a body motion determining step S24 for determining the body motion of the subject by using the standard deviation found in the standard deviation calculating step S22, and the amplitude of the respiratory waveform drawn in the respiratory waveform drawing step S23, a twitch determining step S25 for determining whether or not the body motion of the subject S is a twitch, a respiratory rate estimating step S26 for estimating and outputting the respiratory rate of the subject on the basis of the respiratory waveform drawn in the respiratory waveform drawing step S23, and a display step S27 for displaying the outputted respiratory rate.

The load detecting step S21, the standard deviation calculating step S22, the respiratory waveform drawing step S23, the body motion determining step S24, and the display step S27 are substantially (practically) the same, respectively, as the load detecting step S11, the standard deviation calculating step S12, the respiratory waveform drawing step S13, the body motion determining step S14, and the display step S16 which are carried out by the biological state monitoring system 100 of the first embodiment. Therefore, explanations therefor will be omitted.

[The Twitch Determining Step and the Respiratory Rate Estimating Step]

In the twitch determining step S25, the twitch determining unit 35 determines whether or not the body motion arising in the subject S is a twitch on the basis of the determination result of the body motion determining unit 33. In particular, the determination is performed by the following method.

The twitch determining unit 35 receives the determination result of body motion from the body motion determining unit 33 and, at the point of change from absence of body motion to presence of body motion in the determination result, starts measuring the length of time. Then, the twitch determining unit 35 obtains, by a measurement, a length of time (duration, duration time) from the time point at which the determination result of the body motion determining unit 33 changes from absence of body motion to presence of body motion until the time point at which the determination result return to absence of body motion, and compares the found duration time to a predetermined threshold value $D_{th}$.

As a result of the comparison, in a case that the duration of a certain body motion is shorter than the threshold value $D_{th}$, then this body motion is determined as a twitch of which duration is short. On the other hand, in a case that the duration of a certain body motion is longer than the threshold value $D_{th}$, then this body motion is determined as not a twitch but a body motion of which duration is long.

The threshold value $D_{th}$ used for the determination may be set as appropriate on the basis of the duration of an ordinary twitch. Further, the threshold value $D_{th}$ may be set by considering such a time, as extending until a vibration, which arose in the bed and the like from the influence of a twitch, comes to an end. Alternatively, the threshold value $D_{th}$ may be set by considering other factors with an actual installation of the system. The threshold value $D_{th}$ may be about 0.5 seconds to 6 seconds, in particular for example.

In the present specification and in the present invention, a body motion whose duration is shorter than a predetermined time period or, in other words, a body motion of which occurrence affects the body motion determination for a time period shorter than a predetermined time period (0.5 to 6 seconds for example) is regarded as a twitch.

In the respiratory rate estimating step S26, the respiratory rate estimating unit 34 calculates and outputs the estimated value of the respiratory rate of the subject S, on the basis of the respiratory waveform BW drawn by the respiratory waveform drawing unit 32, the determination result given by the body motion determining unit 33, and the determination result given by the twitch determining unit 35.

The respiratory rate estimating unit 34 receives the respiratory waveform BW from the respiratory waveform drawing unit 32 and the determination result from the body motion determining unit 33, and use these two items with a delay of a predetermined time X. The reason for such a delay will be described later on.

Figure 11:
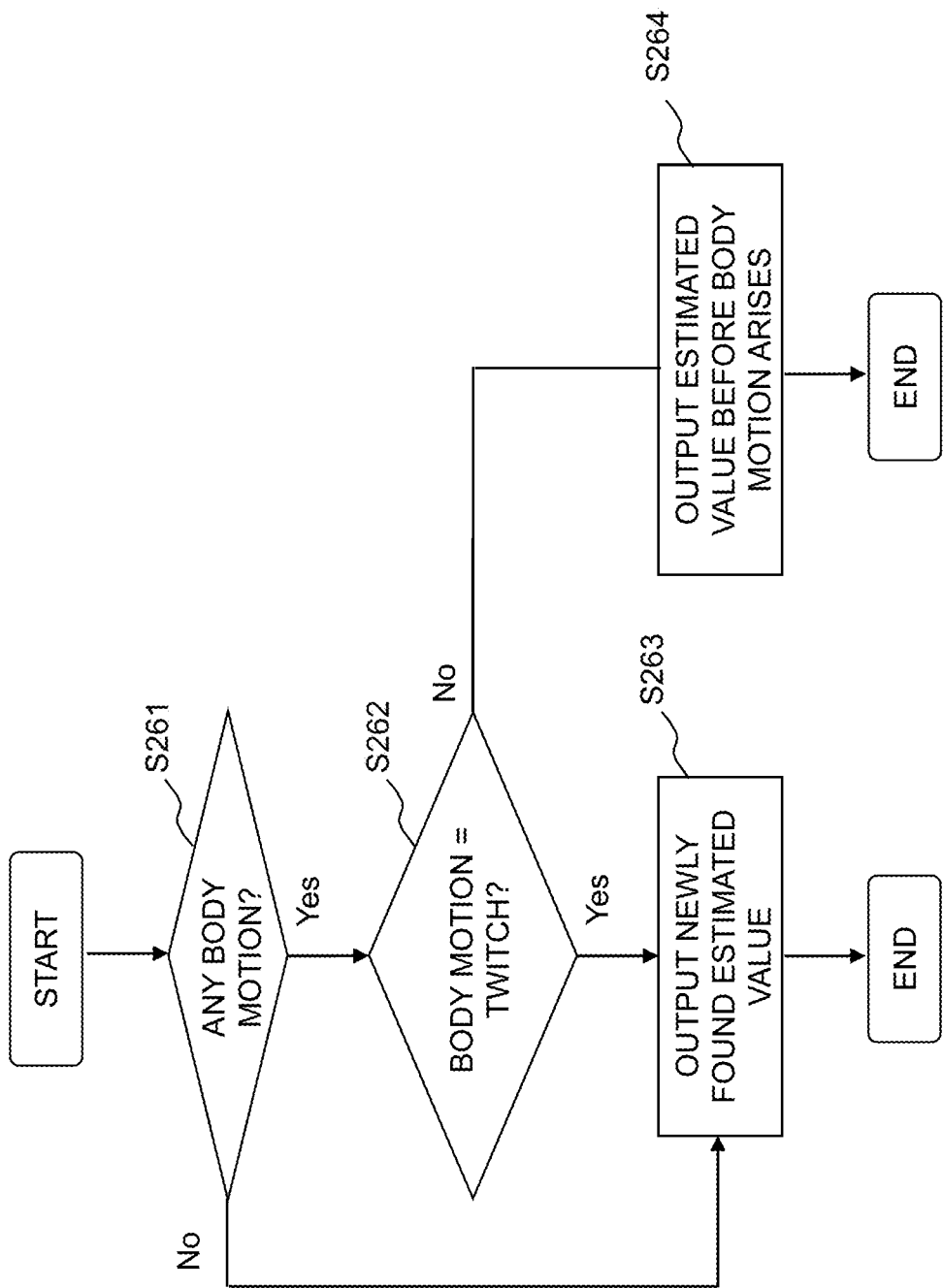
FIG. 11 is a flow chart depicting sub-steps, in the respiratory rate estimating step of the second embodiment, for varying the contents of an estimated value to be outputted on the basis of whether or not the subject's body motion is a twitch.

As depicted in the flow chart of FIG. 11, the respiratory rate estimating unit 34 first determines whether or not there is a body motion arising in the subject S on the basis of the determination result by the body motion determining unit 33 (S261, FIG. 11). Then, if there is no body motion arising in the subject S (S261: No), then the respiratory rate estimating unit 34 outputs the estimated values R calculated successively anew by the Formulas 2 and 3, to the display unit 5 in sequence as the estimated respiratory rate (S263, FIG. 11).

If there is a body motion arising in the subject S (S261: Yes), then the respiratory rate estimating unit 34 carries out the following process, which is different from the respiratory rate estimating step S15 of the first embodiment.

At the point when the determination result by the body motion determining unit 33 changes from absence of body motion to presence of body motion, the respiratory rate estimating unit 34 first determines whether or not the body motion is a twitch on the basis of the determination result by the twitch determining unit 35 (S262, FIG. 11).

Then, if the body motion is not a twitch (S262: No), the respiratory rate estimating unit 34 outputs the estimated value (the first estimated value) R, calculated right before the transition from the resting period to the body motion period, to the display unit 5 as the estimated respiratory rate, instead of the estimated value R of the respiratory rate calculated successively by using the Formulas 2 and 3 (S264, FIG. 11), like the process in the respiratory rate estimating step S15 of the first embodiment performed when there is a body motion arising in the subject S. The process after the subsequent shift from the body motion period to the resting period is also the same as the process performed in the respiratory rate estimating step S15 of the first embodiment.

On the other hand, if the body motion is a twitch (S262: Yes), then in the same manner as for the resting period, the respiratory rate estimating unit 34 successively outputs the estimated values R calculated anew by using the Formulas 2 and 3, to the display unit 5 as the estimated respiratory rates (S263, FIG. 11). That is, the respiratory rate estimating unit 34 is configured such that, even if the body motion determining unit 33 determines that there is a body motion arising in the subject S, provided that the twitch determining unit 35 determines that the body motion is a twitch, the respiratory rate estimating unit 34 carries out the same process as for the resting period without regarding the period of the arising body motion as a body motion period.

Note that as described earlier on, the respiratory rate estimating unit 34 uses the respiratory waveform BW received from the respiratory waveform drawing unit 32 and the body motion determination result received from the body motion determining unit 33, with a delay of the predetermined time X. Therefore, if the predetermined time X is larger than the threshold value $D_{th}$, then at the point when the determination result by the body motion determining unit 33 changes from absence of body motion to presence of body motion in the process carried out by the respiratory rate estimating unit 34, the twitch determining unit 35 is already finished with the determination of whether or not the body motion is a twitch. Therefore, as described above, the respiratory rate estimating unit 34 can determine (confirm) whether or not the body motion is a twitch at the point when the determination result by the body motion determining unit 33 changes from absence of body motion to presence of body motion.

Figure 12:
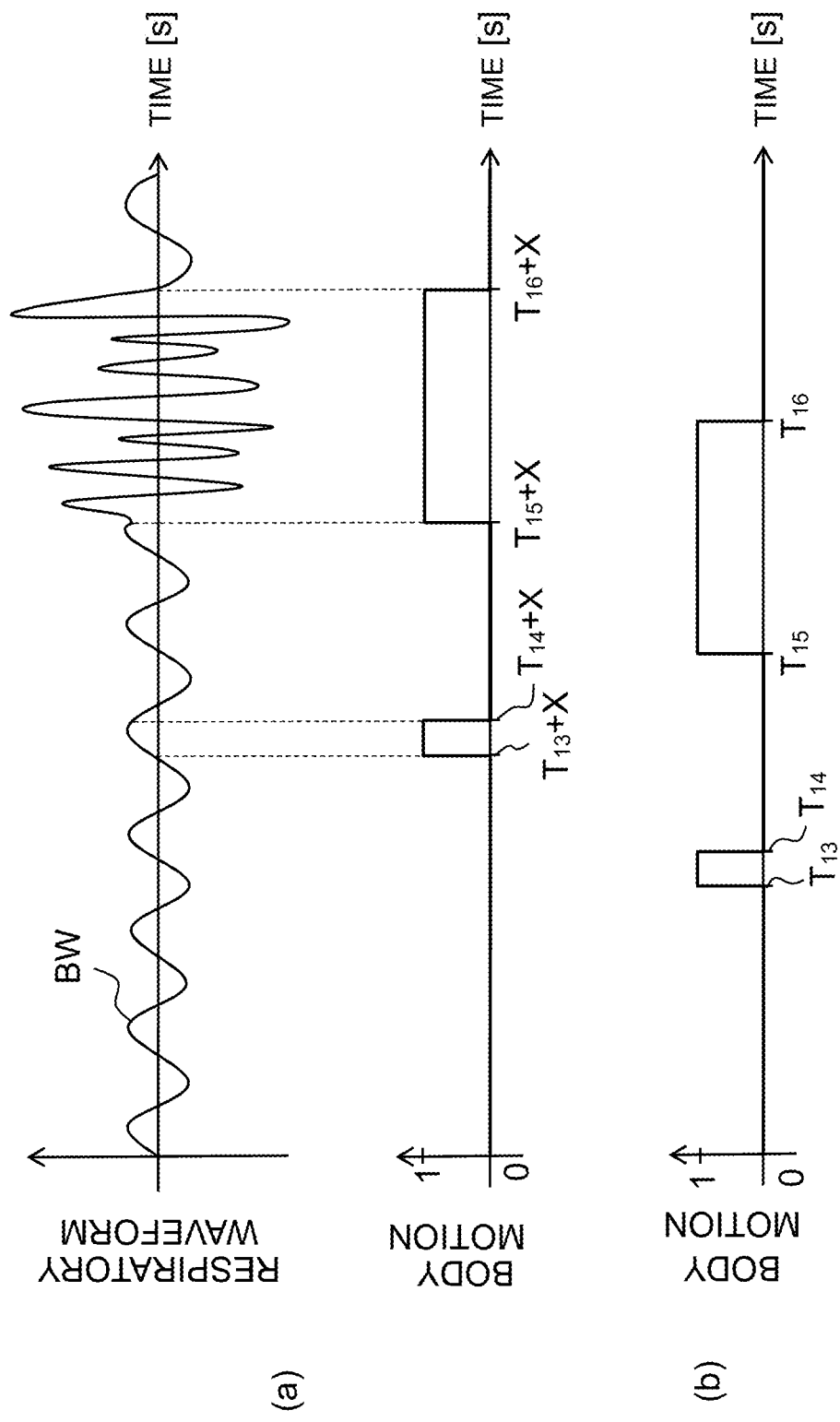
FIGS. 12(a) and 12(b) are illustrative views for explaining a step for performing an adjustment of the estimated value of the respiratory rate to be outputted by the respiratory rate estimating unit, with reference to a determination result of a twitch determining unit.

FIGS. 12(a) and 12(b) will be used to explain a particular example of this process. Note that in the lower graph of FIG. 12(a), and in FIG. 12(b), "1" means presence of body motion and "0" means absence of body motion, on the vertical axis.

As depicted in FIG. 12(b), in a case that the body motion determining unit 33 determines that the subject S has a body motion at a time $T_{13}$, then the twitch determining unit 35 measures the duration (continuance time) from that point to a time $T_{14}$ when the determination result by the body motion determining unit 33 returns to absence of body motion again, and compares the found duration to the threshold value $D_{th}$. Here, the threshold value $D_{th}$ is 3 seconds, and the duration from the time $T_{13}$ to the time $T_{14}$ is 2 seconds. Therefore, the twitch determining unit 35 determines that the body motion arising over the period from the time $T_{13}$ to the time $T_{14}$ is a twitch.

Then, as depicted in the lower graph of FIG. 12(a), after the predetermined time X (the data delay time for the respiratory rate estimating unit 34: 5 seconds or so for example) has elapsed since the time $T_{13}$, that is, at the time $T_{13}+X$, the respiratory rate estimating unit 34 determines the contents of the following process with reference to the determination result by the twitch determining unit 35, on the basis of the determination result by the body motion determining unit 33 stating that there is a body motion arising in the subject S.

In this context, because the twitch determining unit 35 has determined that the body motion arising from the time $T_{13}$ to the time $T_{14}$ is a twitch, even after the time $T_{13}+X$, the respiratory rate estimating unit 34 successively outputs the estimated value R calculated anew by using the Formulas 2 and 3 to the display unit 5, as the estimated respiratory rate. The estimated value indicates the state of the subject S around the time $T_{13}$, and is outputted after the time 113+X, that is, being delayed by the predetermined time X.

Note that as depicted in the upper graph of FIG. 12(a), during the period when there is a twitch arising in the subject S, there is no large disturbance arising in the respiratory waveform of the subject S. Therefore, even if the sampling time period for estimation contains a period when there is a twitch arising, there is still a high reliability of the estimated value R calculated anew by using the Formulas 2 and 3.

Subsequently, if the body motion determining unit 33 determines that there is a body motion arising in the subject S at a time $T_{15}$, then the twitch determining unit 35 restarts to measure the time from that point. Then, the twitch determining unit 35 determines that the body motion is not a twitch at the point when the period, for which the the body motion determining unit 33 has determined as "presence of body motion" exceeds the threshold value $D_{th}$ (3 seconds in this case). In this context, it is assumed that the body motion determining unit 33 has determined that the body motion arising continuously from the time $T_{15}$ is not a twitch, prior to the time $T_{15}+X$.

Then, at the time $T_{15}+X$, that is, after the predetermined time X has elapsed since the time $T_{15}$, the respiratory rate estimating unit 34 determines the contents of the following process with reference to the determination result by the twitch determining unit 35 again, on the basis of the determination result by the body motion determining unit 33 stating that there is a body motion arising in the subject S.

In this context, because the twitch determining unit 35 has determined that the body motion arising continuously from the time $T_{15}$ is not a twitch, after the time $T_{15}+X$, the respiratory rate estimating unit 34 outputs the estimated value R calculated right before the time $T_{15}+X$, to the display unit 5 as the estimated respiratory rate. While the estimated value indicates the state of the subject S after the time $T_{15}$, it is outputted after the time $T_{15}+X$ with a delay of the predetermined time X.

The biological state monitoring system 200 of the second embodiment has the following effects in addition to the effects of the biological state monitoring system 100 of the first embodiment.

The biological state monitoring system 200 of the second embodiment includes the twitch determining unit 35 such that even if there is a body motion arising in the subject S, provided that the body motion is a twitch which exerts a small influence on calculating the estimated value of the respiratory rate, the respiratory rate estimating unit 34 is caused to keep on outputting the estimated value R calculated anew. In this manner, the biological state monitoring system 200 of the second embodiment can shorten the period in which the estimated value calculated in the past resting period is outputted alternatively to a minimum (bare minimum), by determining whether or not the body motion is a twitch. Therefore, it is possible to output the estimated value of the respiratory rate of the subject with higher reliability.

Note that the respiratory rate estimating unit 34 of the biological state monitoring system 200 of the above second embodiment carries out the process for the respiratory waveform BW received from the respiratory waveform drawing unit 32 and the body motion determination result received from the body motion determining unit 33, with a delay of the predetermined time X. However, without being limited to that, for example, depending on the processing contents in the system, the respiratory waveform BW may be drawn a predetermined length of time later than the body motion is determined by the body motion determining unit 33. In this case, even without the respiratory rate estimating unit 34 purposely applying a delay, it is still possible for the twitch determining unit 35 to finish the determination before the process is carried out by the respiratory rate estimating unit 34.

Modified Embodiments

It is also possible for the biological state monitoring systems 100 and 200 of the above embodiments to adopt the following modified embodiments.

The respiratory rate estimating unit 34 of the biological state monitoring systems 100 and 200 of the above embodiments may be configured to maintain the estimated value of the respiratory rate for output at the estimated value R calculated right before the body motion period only within the body motion period, after it is determined that there is a body motion arising in the subject S. The body motion period may continue as long as the body motion is arising in the subject S, and thus may extend over a longtime period. On the other hand, the predetermined period after a body motion comes to an end is the sampling period for estimation or so at the longest and, in the above first and second embodiments, is about 25 seconds. Therefore, as in this modified embodiment, even if it is configured to adjust the estimated value to be outputted by the respiratory rate estimating unit 34 only within the body motion period, it is still possible to suppress the influence of the body motion of the subject S to a considerable degree, thereby outputting the estimated value of the respiratory rate of the subject with high reliability.

The biological state monitoring systems 100 and 200 of the above embodiments may cease to output the estimated value of the respiratory rate of the subject S in the body motion period and/or the predetermined initial period of the resting period right after the body motion period, after a body motion is determined as arising in the subject S. In such a case, the users of the biological state monitoring systems 100 and 200 can predict the estimated value of the current respiratory rate of the subject by memorizing the estimated value of the respiratory rate outputted last (that is, the estimated value R calculated right before the body motion period), for example. According to the configuration of this modified embodiment, it is also possible to suppress the influence of the body motion of the subject S, thereby outputting the estimated value of the respiratory rate of the subject with high reliability.

In the biological state monitoring systems 100 and 200 of the above embodiments, the respiratory rate estimating unit 34 may estimate the respiratory rate of the subject S without using the respiratory waveform BW.

In particular, for example, the respiratory rate estimating unit 34 calculates the respiratory rate of the subject S by carrying out the Fourier analysis on at least one of the load signals $s_1$ to $s_4$ corresponding to the predetermined sampling period so as to specify the peak frequency coming up in the frequency band corresponding to the respirations (from about 0.2 Hz to about 0.33 Hz because the human respiration is performed about 12 to 20 times per minute). With the specified peak frequency, it is possible to calculate (estimate) the respiratory rate of the subject S over that period.

In this case, too, if the sampling period includes a body motion period, then the reliability of the calculated respiratory rate (estimated value) of the subject S may decrease due to a variation of the load signals $s_4$ to $s_4$ arising from the body motion. Therefore, it is possible to raise the reliability of the estimated value of the respiratory rate by adjusting the outputted value by the same method as used by the respiratory rate estimating unit 34 of the above embodiments.

In the biological state monitoring systems 100 and 200 of the above embodiments, the body motion determining unit 33 normalizes the standard deviations $\sigma_1$ to $\sigma_4$ by dividing the standard deviations $\sigma_4$ to $\sigma_4$ by the average amplitude $A_{AVn}$ to reduce (compensate; correct) the influence on the values of the standard deviations $\sigma_1$ to $\sigma_4$, exerted by the frame and/or respiratory depth of the subject S. However, the compensating (correcting) method by utilizing the amplitude of the respiratory waveform BW is not limited to that. In particular, for example, the standard deviations $\sigma_1$ to $\sigma_4$ may be normalized by way of dividing the same by the latest amplitude $A_n$ of the respiratory waveform BW.

Note that, it is also possible to compensate the threshold value by using the amplitude of the respiratory waveform BW and compare the standard deviations $\sigma_1$ to $\sigma_4$ to the compensated threshold value, instead of compensating the standard deviations $\sigma_1$ to $\sigma_4$ by using the amplitude of the respiratory waveform BW and then comparing the compensated values to the threshold value. In particular, for example, in the above embodiments, instead of dividing the standard deviations $\sigma_1$ to $\sigma_4$ by the average amplitude $A_{AVn}$, it is possible to perform a desired compensation (correction) by multiplying the predetermined threshold value by the average amplitude $A_{AVn}$. In this manner, the two methods mentioned above are practically equivalent and thus it is possible to appropriately select either the standard deviations or the threshold value used in the comparison for the compensation (correction) by the amplitude of the respiratory waveform. In the present specification and in the present invention, the expression "compensating the standard deviations by the amplitude of the respiratory waveform" is termed to include compensating the threshold value by the amplitude of the respiratory waveform.

In the biological state monitoring systems 100 and 200 of the above embodiments, the body motion determining unit 33 performs the body motion determination by the comparison between the simple average $\sigma s_{AV}$ of the normalized standard deviations $\sigma s_1$ to $\sigma s_4$ and the threshold value $\sigma s_{TH}$. However, it is also possible to determine the body motion by a comparison between at least one of the normalized standard deviations $\sigma s_1$ to $\sigma s_4$ and the threshold value, a comparison between simple average values of at least two or more of the normalized standard deviations $\sigma s_1$ to $\sigma s_4$ and the threshold value, a comparison between the total value of at least two or more of the normalized standard deviations $\sigma s_1$ to $\sigma s_4$ and the threshold value, or the like.

Further, in the biological state monitoring systems 100 and 200 of the above embodiments, it is also capable for the body motion determining unit 33 to use a variance which is the squared standard deviation instead of the standard deviation. If the variance is normalized by the amplitude of the respiratory waveform, then the variance may be divided by the squared amplitude of the respiratory waveform. Therefore, in the present specification and in the present invention, the standard deviation is termed to include the variance.

The body motion determining unit 33 may provide the threshold value used for the body motion determination with hysteresis. In particular, for example, with a first threshold value and a second threshold value larger than the first threshold value set in advance, under the condition that the subject S is determined as with no body motion arising therein, as far as the simple average $\sigma s_{AV}$ is yet smaller than the second threshold value, the subject S is not determined as with a body motion arising therein. On the other hand, under the condition that the subject S is determined as with a body motion arising therein, even if the simple average $\sigma s_{AV}$ is smaller than the second threshold value, the subject S is not determined as with no body motion arising therein, but is determined as with no body motion arising therein at the point of the simple average $\sigma s_{AV}$ becoming smaller than the first threshold value.

In the biological state monitoring systems 100 and 200 of the above embodiments, the body motion determining unit 33 may determine whether or not the subject S has a body motion on the basis of a comparison between at least one of the standard deviations $\sigma_1$ to $\sigma_4$ and the threshold value, or a comparison between the total value or a simple average of at least two or more of the standard deviations $\sigma_1$ to $\sigma_4$ and the threshold value, without finding the normalized standard deviations $\sigma s_1$ to $\sigma s_4$.

In the biological state monitoring systems 100 and 200 of the above embodiments, the body motion determining unit 33 can also determine whether or not the subject S has a body motion without using the standard deviations $\sigma_1$ to $\sigma_4$. In particular, for example, it determines whether or not the subject S has a body motion on the basis of a movement of the center of gravity of the subject S.

As described earlier on, the center of gravity G of the subject S oscillates in the direction of the body axis SA of the subject S according to the respirations of the subject S (FIG. 5(a)). Further, the center of gravity G of the subject S moves according to that if the subject S has a small body motion or a large body motion. Then, the moving distance of the center of gravity G over a predetermined period increases in the ascending order of the period when the subject S only respires, the period when the subject S has a small body motion, and the subject S has a large body motion.

Therefore, the body motion determining unit 33 can determine whether or not the subject S has a body motion by comparing a predetermined threshold value with the moving distance of the center of gravity G over a predetermined period. In particular, for example, it is possible to determine that the subject S has a small body motion if the moving distance d of the center of gravity G over a predetermined period is longer than a threshold value $d_{th}$.

The biological state monitoring systems 100 and 200 of the above embodiments do not need to include all of the load detectors 11 to 14 but may include only any one of the four. For example, if there are three such load detectors, then it is still possible to detect the position of the center of gravity G of the subject S on the plane of the bed BD provided that the three load detectors are not arranged on a straight line. Further, the load detectors do not need to be arranged at the four corners of the bed but may be arranged in any positions as far as they can detect the load of the subject on the bed and the variation thereof. Further, the load detectors 11 to 14 are not limited to load sensors using beam-type load cells but, for example, force sensors are also usable.

Figure 13:
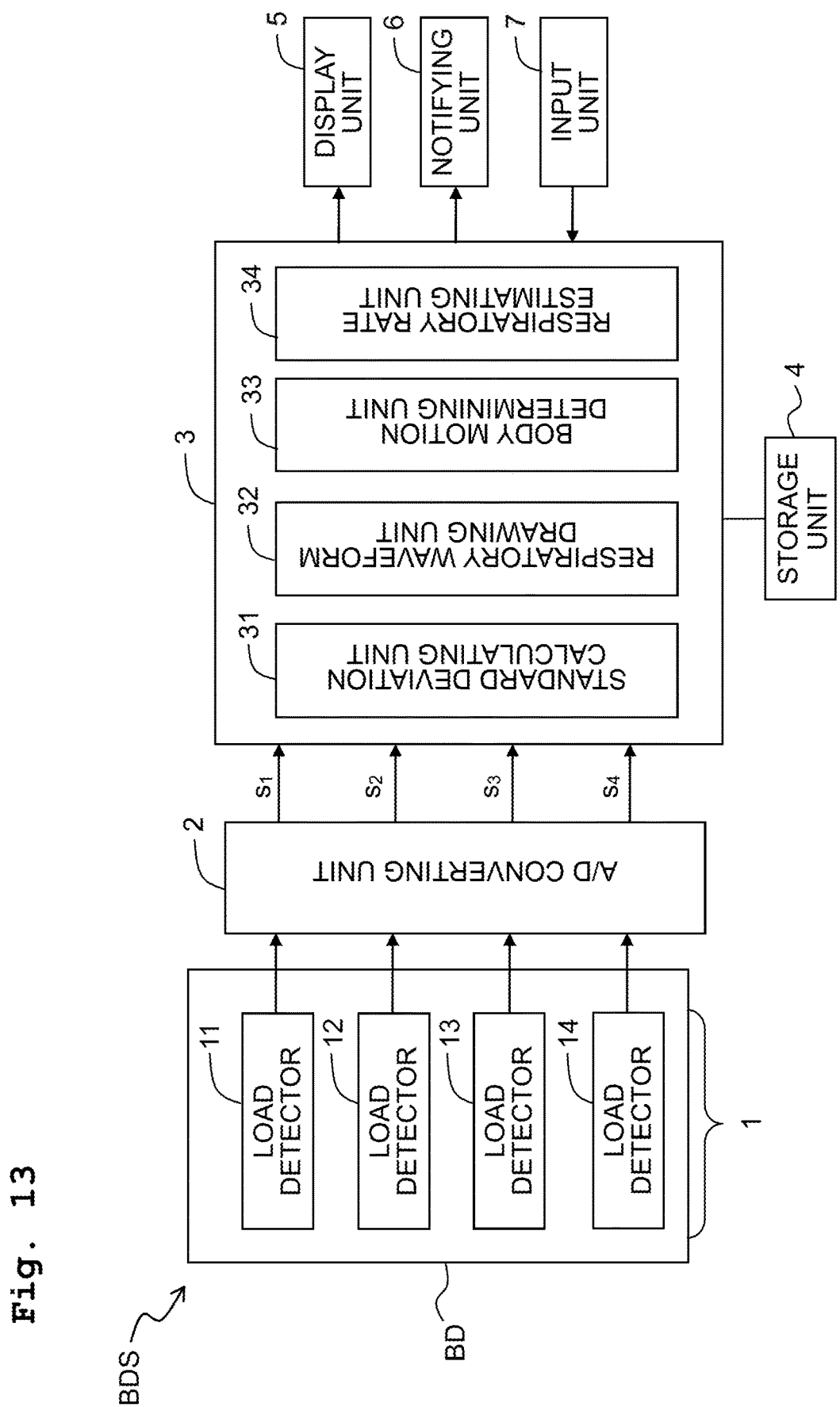
FIG. 13 is a block diagram depicting an overall configuration of a bed system according to a modified embodiment of the present invention.

In the biological state monitoring systems 100 and 200 of the above embodiments, the load detectors 11 to 14 are arranged respectively on the undersides of the casters C attached to the lower ends of the legs of the bed BD. However, there is no limitation thereto. Each of the load detectors 11 to 14 may be provided respectively between one of the four legs of the bed BD and the board of the bed BD. Alternatively, if each of the four legs of the bed BD can be divided into upper and lower portions, each of the load detectors 11 to 14 may be provided between the upper leg and the lower leg. Further alternatively, the load detectors 11 to 14 may be formed integral with or removable from the bed BD to construct a bed system BDS comprising the bed BD, and the biological state monitoring system 100 or 200 of the first or second embodiment (FIG. 13).

In the biological state monitoring systems 100 and 200 of the above embodiments, between the load detecting unit 1 and the A/D converting unit 2, it is possible to provide a signal amplifying unit to amplify the load signals fed from the load detecting unit 1, and a filtering unit to eliminate the noises from the load signals.

In the biological state monitoring systems 100 and 200 of the above embodiments, the display unit 5 may include a printer for printing out the information indicating the biological state (respiratory rate, presence or absence of body motion, etc.), a simplified visual display means such as lamps indicating the biological state (respiratory rate, presence or absence of body motion, etc.), and/or the like, instead of the monitor or in addition to the monitor. Further, the notifying unit 6 may include a vibration generating unit for performing the notification by way of vibration, instead of the speaker or in addition to the speaker.

The present invention is not limited to the embodiments described above provided that the feature of the present invention is maintained. Other embodiments, which are conceivable within the scope of the technical concept of the present invention, are also included in the scope of the present invention.

INDUSTRIAL APPLICABILITY

According to the biological state monitoring system of the present invention, it is possible to suppress the influence of body motion of the subject so as to estimate the respiratory rate of the subject with high precision. Therefore, by using the biological state monitoring system of the present invention, it is possible to provide high-quality medical treatments and caregiving services on the basis of the high-precision estimation of the respiratory rate.

PARTS LIST

1: load detecting unit, 11, 12, 13, 14: load detector, 2: A/D converting unit, 3: control unit, 31: standard deviation calculating unit, 32: respiratory waveform drawing unit, 33: body motion determining unit, 34: respiratory rate estimating unit, 35: twitch determining unit, 4: storage unit, 5: display unit, 6: notifying unit, 7: input unit, 100: biological state monitoring system, BD: bed, BDS: bed system, S: subject.

The invention claimed is:

1. A biological state monitoring system for monitoring a biological state of a subject on a bed, the system comprising:
  at least one load detector configured to detect a load of the subject on the bed; and
  a controller configured to:
  determine whether or not the subject has a body motion, based on a temporal variation of a detection value of the load detector;
  successively obtain and output estimated values of respiratory rate of the subject, based on the temporal variation of the detection value of the load detector; and
  determine whether or not the body motion is a twitch, based on a duration of the body motion of the subject,
  wherein in a case that the controller determines that the body motion is not a twitch, the controller ceases to output the estimated value of the respiratory rate, or outputs a first estimated value which is the latest among the estimated values obtained in a first period, the first period being directly preceding the body motion and being determined by the controller to be a period in which the subject has no body motion, and in a case that the controller determines that the body motion is a twitch, the controller successively outputs newly obtained estimated values of the respiratory rate.

2. The biological state monitoring system according to claim 1, wherein in the case that the controller determines that the body motion is not a twitch, the controller outputs the first estimated value.

3. The biological state monitoring system according to claim 1, wherein the controller determines whether or not the body motion of the subject is a twitch, based on a comparison between a predetermined threshold value and a length of a period which is determined by the controller to be a period in which the subject has the body motion.

4. The biological state monitoring system according to claim 1, further comprising a display configured to display the estimated value of the respiratory rate of the subject, outputted by the controller.

5. A bed system comprising:
a bed; and
the biological state monitoring system according to claim 1.

* * * * *